US011292816B2

(12) United States Patent
Steinhagen et al.

(10) Patent No.: US 11,292,816 B2
(45) Date of Patent: Apr. 5, 2022

(54) ASSAY FOR THE DIAGNOSIS OF VIRAL INFECTIONS

(71) Applicant: EUROIMMUN Medizinische Labordiagnostika AG, Luebeck (DE)

(72) Inventors: Katja Steinhagen, Gross Groenau (DE); Marc Pollmann, Luebeck (DE); Claudia Messing, Klempau (DE); Oliver Klemens, Luebeck (DE); Jana Boethfuer, Schlagsdorf (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 23 days.

(21) Appl. No.: 15/733,517

(22) PCT Filed: Feb. 22, 2019

(86) PCT No.: PCT/EP2019/054469
§ 371 (c)(1),
(2) Date: Aug. 18, 2020

(87) PCT Pub. No.: WO2019/162454
PCT Pub. Date: Aug. 29, 2019

(65) Prior Publication Data
US 2020/0385430 A1 Dec. 10, 2020

(30) Foreign Application Priority Data

Feb. 22, 2018 (EP) .................................... 18158177
Nov. 23, 2018 (EP) .................................... 18207934

(51) Int. Cl.
| | | |
|---|---|---|
| A61K 39/00 | (2006.01) | |
| A61K 39/12 | (2006.01) | |
| C07K 14/005 | (2006.01) | |
| A61K 39/295 | (2006.01) | |
| A61K 39/395 | (2006.01) | |
| C12N 7/00 | (2006.01) | |
| G01N 33/569 | (2006.01) | |

(52) U.S. Cl.
CPC .............. *C07K 14/005* (2013.01); *C12N 7/00* (2013.01); *G01N 33/56983* (2013.01); *C12N 2770/24122* (2013.01); *G01N 2333/185* (2013.01)

(58) Field of Classification Search
CPC .......... Y02A 50/30; A61P 31/12; A61P 31/14; C07K 14/005; A61K 39/12
See application file for complete search history.

(56) References Cited

U.S. PATENT DOCUMENTS

2019/0383814 A1   12/2019   Steinhagen et al.

FOREIGN PATENT DOCUMENTS

| WO | 02/081754 | 10/2002 |
|---|---|---|
| WO | 2011/062625 | 5/2011 |
| WO | 2015/095735 A2 | 6/2015 |
| WO | 2015/095735 A3 | 6/2015 |
| WO | 2016/022958 | 2/2016 |
| WO | WO2016022958 | * 2/2016 |
| WO | 2017144174 | 8/2017 |

OTHER PUBLICATIONS

International Search Report dated May 31, 2019 in PCT/EP2019/054469.
Written Opinion dated May 31, 2019 in PCT/EP2019/054469.
Partial European Search Report dated May 2, 2018 in European Application No. 18158177.8, 14 pages.
European Search Report dated Jun. 25, 2018 in European Application No. 18158177.8, 14 pages.
Akey et al. "Flavivirus NS1 crystal structures reveal a surface for membrane association and regions of interaction with the immune system," Science, Feb. 21, 2014; 343(6173): 881-885, 10 pages.
Frost et al., "Serologic Evidence of Powassan Virus Infection in Patients with Suspected Lyme Disease," Emerging Infectious Diseases, vol. 23. No. 8, Aug. 2017, pp. 1384-1388.
Hermance et al., "Pawassan Virus: An Emerging Arbovirus of Public Health Concern in North America," Vector-Borne and Zoonotic Diseases, vol. 17, No. 7, 2017, pp. 453-452.
Platt et al., "Zika virus-related neurotropic flaviviruses infect human placental explants and cause fetal demise in mice," Sci. Transl. Med. 10, eaao7090 (2018), pp. 1-10.
Thomm at al., "Development and Validation of a Serologic Test Panel for Detection of Powassan Virus Infection in U.S. Patients Residing in Regions Where Lyme Disease is Endemic," mSphere, Jan./Feb. 2018, vol. 3, Issue 1, e00467-17, pp. 1-10.
Tokarz et al., "A multiplex serologic platform for diagnosis of tick-borne diseases," Scientific Reports (2018) 8:3158, pp. 1-10.

(Continued)

*Primary Examiner* — Barry A Chestnut
(74) *Attorney, Agent, or Firm* — Grüneberg and Myers PLLC

(57) ABSTRACT

A recombinant or chemically synthesized polypeptide includes SEQ ID NO: 1 or a variant thereof. A diagnostically useful carrier includes means for specifically capturing an antibody to SEQ ID NO: 1 in a sample from a subject. A kit includes the polypeptide or the diagnostically useful carrier. A method for diagnosing, prognosing, or monitoring the treatment of a virus, preferably Flavivirus, more preferably POWV infection includes detecting in the sample from a subject the presence or absence of an antibody to SEQ ID NO: 1 and/or an antibody to SEQ ID NO: 2. A polypeptide including SEQ ID NO: 1 and/or SEQ ID NO: 2, and/or a variant thereof is useful for the diagnosis. An IgM antibody to SEQ ID NO: 1 or means for specifically capturing an IgM class antibody to SEQ ID NO: 1 is useful for increasing the diagnostic reliability of an immunoassay for the diagnosis of a virus infection.

20 Claims, 4 Drawing Sheets

Specification includes a Sequence Listing.

(56) References Cited

OTHER PUBLICATIONS

Wong et al., *"Zika virus infection—the next wave after dengue?,"* Journal of the Formosan Medical Association (2016) 115, 226-242.
Xu et al., *"Contribution of intertwined loop to membrane association revealed by Zika virus full-length NS1 structure,"* The EMBO Journal (2016) 35: 2170-2178.

* cited by examiner 8-16% denat. iD-PAGE, Coomassie identification with MALDI-TOF

Fig. 1

8-16% denat. iD-PAGE, Coomassie identification with MALDI-TOF

Fig. 2

ASSAY FOR THE DIAGNOSIS OF VIRAL INFECTIONS

CROSS-REFERENCE TO RELATED APPLICATIONS

This application is the National Stage entry under § 371 of International Application No. PCT/EP2019/054469, filed on Feb. 22, 2019, and which claims the benefit of European Application No. 18158177.8, filed on Feb. 22, 2018 and European Application No. 18207934.3, filed on Nov. 23, 2018. The content of each of the applications is hereby incorporated by reference in its entirety.

REFERENCE TO A SEQUENCE LISTING

The instant application is accompanied by an ASCII text file which has been submitted via EFS-Web as a computer readable form containing the sequence listing, titled "2020-08-25-Sequence-Listing-ST25.txt", created on Aug. 25, 2020, with a file size of 87,911 bytes, is hereby incorporated by reference in its entirety.

BACKGROUND OF THE INVENTION

Field of the Invention

The present invention relates to a recombinant or chemically synthesized polypeptide comprising SEQ ID NO: 1 or a variant thereof, a diagnostically useful carrier comprising in means for specifically capturing an antibody to SEQ ID NO: 1 in a sample from a subject, a kit comprising the polypeptide or a diagnostically useful carrier, and a method for diagnosing, prognosing or monitoring the treatment of a virus, preferably Flavivirus, more preferably POWV infection comprising the step detecting in the sample from a subject the presence or absence of an antibody to SEQ ID NO: 1 and/or an antibody to SEQ ID NO: 2, and a use of a polypeptide comprising SEQ ID NO: 1 and/or a SEQ ID NO: 2 or a variant thereof for the diagnosis and a use of an IgM antibody to SEQ ID NO: 1 or in means for specifically capturing an IgM class antibody to SEQ ID NO: 1 for increasing the diagnostic reliability of an immunoassay for the diagnosis of a virus infection.

Description of Related Art

Tick-borne diseases are a major public health concern for the great Great Lakes region of the mid-Eastern United States to the sub-Saharan deserts of Africa. Ticks carry agents cause a wide array of clinical pathologies which are protozoan bacterial or viral in origin. Among them is the Powassan virus (POWV), which was first reported in 1958 in Powassan, Ontario, US. POWV is endemic in the northeast and upper mid-west of the United States, and cases have also been reported in far-eastern Russia. Like other tick-borne diseases, POWV is a diagnostic challenge because of its versatility of clinical presentation and the unpredictability of the cause of the illness.

The symptoms of POWV infection vary from person to person, as some are asymptomatic and others have a more progressive cause, meaning that a significant number, possibly the majority of patients remain undiagnosed. However, a POWV infection not recognized as such can develop to a rapidly progressing, neurological disease. Symptoms include headache, fever, focal neurological deficits, confusion, generalized weakness, ataxia, somnolence, speech problems, aphasia and dysarthria. The fatality rate is 10%, and about 50% of those people who developed neurological symptoms end up with long-term deficits.

Among the entirety of Flaviviruses, POWV, according to phylogenetic analyses based on the sequences of glycoprotein E (GpE) and non-structural protein 1 (NS1), is one of the more distant relatives of the ZIKV (Wong, S. S., Poon, R. W., Wong, S. C. (2016) Zika virus infection—the next wave after dengue?, Journal of the Formosan Medical Association, http://doi.org/10.1016/j.jfma.2016.02.002).

Moreover, it has been assigned to the group of tick-borne Flaviviruses rather than to the group of mosquito-borne Flaviviruses including ZIKV (Mackenzie, J., Williams, D. T. (2009) The Zoonotic Flaviviruses of Southern, South-Eastern and Eastern Asia, and Australasia: The Potential for Emergent Viruses, Zoonoses and Public Health, 56(6-7), 338-56).

Unfortunately, it appears to share with the ZIKV the capacity for transplacental transmission, as well as subsequent infection and injury to the developing fetus (Platt, D. J., Smith, A. M., Arora, N., Diamond, M. S., Coyne, C. B., Miner, J. J. (2018) Zika virus-related neurotropic Flaviviruses infect human placental explants and cause fetal demise in mice, Science Translational Medicine, 10 (426)).

The diagnosis of tick-borne diseases such as POWV infection represents a clinical challenge. Imaging methods including computer tomography (CT) scans and magnetic resonance imaging (MRI) of the brain may be employed. However, acute presentations of POWV will show no abnormalities on a CT scan unless there is intraparenchymal beating and subdural hematoma. MRI cannot be employed in an emergency setting as it requires a patient to be still throughout the scan. No imaging method at present may be used to provide the specific diagnosis of an infectious disease.

According to several reports, no test for the specific diagnosis of a POWV infection based on the detection of specific antibodies is commercially available by now. Thomm et al. (2018) use a commercial anti-TBEV ELISA IgG and IgM tests that employ inactivated TBEV antigens of strain K23 in addition to an indirect fluorescence assay based on Vero cells infected with POWV (Thomm, A. M., Schotthoefer, A. M., Dupuis, II, A. P., Kramer, L. D., Frost, H. M., Fritsche, T. R., Harrington, Y. A., Know, K. K., Kehl, S. C. (2018) Development and Validation of a Serologic Test Panel for Detection of Powassan Virus Infection in U.S. Patients Residing in Regions Where Lyme Disease Is Endemic, mSphere, 3(1), e00467-17). The authors report an overall test panel sensitivity of 89%.

Frost et al. (2017) performed a West Nile virus enzyme immunoassay, a Flavivirus mosaic panel and an IgG IFA assay panel including tests for TBEV, WNV, yellow fever virus, Dengue viruses 1-4, and Japanese encephalitis viruses on samples positive for POWV IgG by the IFA assay (Frost, H. M., Schotthoefer, A. M., Thomm A. M., Dupuis, II, A. P., Kehl, S. C., Kramer, L. D., Fritsche, T. R., Harrington, Y. A., Know, K. K. (2017) Serologic Evidence of Powassan Virus Infection in Patients with Suspected Lyme Disease, 23 (8), 1384-1388).

The state of the art discloses a range of diagnostic tests centering around the detection of antibodies to Flavivirus NS1 and GpE polypeptides from Flaviviruses other than POWV.

The Anti-West Nile Virus ELISA (IgM) (product no. EI 2662-9601 M) commercialized by EUROIMMUN Medizinische Labordiagnostika, Lubeck, Germany is based on the detection of WNV IgM antibodies to WNV GpE. The manufacturer's instructions disclose that significant cross reactivity with IgM to GpE from various other pathogens is an issue. For example, approximately 25% of sera from patients suffering from Dengue virus infection were tested positive.

WO2017/144174 discloses the detection of antibodies to SEQ ID NO: 2, but not to SEQ ID NO: 1.

WO2017/174193 discloses a diagnostic carrier for the detection of ZIKV comprising a ZIKV GpE and a ZKV NS1 antigen. POWV, let alone reagents for the detection of POWV, are not disclosed. It is disclosed that ZKV GpE antigen shows a high cross reactivity towards antibodies to other Flaviviruses.

Tokarz et al. (2018) report a microarray-based test for the simultaneous detection of IgM and IgG antibodies to peptides comprising 12 amino acids derived from POWV GpE. The specificity and sensitivity of the assay, particularly compared to other flavivirus diagnostic assays, were not addressed. The purpose was to distinguish antibody responses to eight major tick-borne pathogens in the US, among them POWV, but no other flavivirus (Sci. Reports 8:3158, doi:10.1038/s41598-018-21349-2). The authors suggest that an ELISA is insufficiently reliable a diagnostic method and should therefore not be used.

BRIEF SUMMARY OF THE INVENTION

Therefore, there is a long-standing need for the provision of a serological assay for the sensitive and specific diagnosis of POWV infection.

A problem underlying the present invention is to provide a serological assay for the diagnosis of a virus, preferably Flavivirus, more preferably POWV infection.

Another problem underlying the present invention is to provide a serological assay for the diagnosis of a virus, preferably Flavivirus, more preferably POWV infection, with excellent diagnostic reliability or increased diagnostically reliability relative to state of the art assays, in particular in terms of specificity and/or sensitivity. Optionally the assay is based on the detection of a single antibody.

Another problem underlying the present invention is to provide methods and reagents for such an assay.

The problem underlying the present invention is solved by the subject-matter of the attached independent dependent claims.

In a first aspect, the problem underlying the present invention is solved by a recombinant or chemically synthesized polypeptide comprising SEQ ID NO: 1 or a variant thereof, preferably in an isolated form.

In a second aspect, the problem underlying the present invention is solved by a diagnostically useful carrier comprising a means for specifically capturing an antibody to SEQ ID NO: 1, and/or a means for specifically capturing an antibody to SEQ ID NO: 2, in a sample from a subject.

In preferred embodiment, the diagnostically useful carrier is selected from the group comprising a bead, preferably a paramagnetic bead, a test strip, a microtiter plate, a membrane, preferably from the group comprising western blot, line blot and dot blot, a lateral flow device, a glass surface, a slide, a microarray, and a biochip.

In a third aspect, the problem is solved by a kit comprising the polypeptide or the diagnostically useful carrier, preferably further comprising a means for specifically detecting a captured antibody to SEQ ID NO: 1 and/or a means for specifically detecting a captured antibody to SEQ ID NO: 2.

In a preferred embodiment, the means for specifically detecting a captured antibody to SEQ ID NO: 1 is a secondary antibody recognizing IgM class antibodies.

In a preferred embodiment, the means for specifically detecting captured antibody to SEQ ID NO: 2 is a secondary antibody recognizing IgG or IgM, preferably IgG class antibodies.

In a preferred embodiment, the kit further comprises a recombinant or monoclonal antibody to SEQ ID NO: 2 and/or a recombinant or monoclonal antibody to SEQ ID NO: 1.

In a fourth aspect, the problem underlying the present invention is solved by a method for diagnosing, prognosing and monitoring the treatment of a virus, preferably Flavivirus, more preferably POWV infection comprising the step detecting in a sample from a subject the presence of an antibody to SEQ ID NO: 1 and/or an antibody to SEQ ID NO: 2, preferably SEQ ID NO: 1.

In a fifth aspect, the problem underlying the present invention is solved by a method for distinguishing a POWV infection from another viral infection, preferably with a Flavivirus other than POWV, comprising the step detecting in a sample from a subject the presence of an antibody to SEQ ID NO: 1 and/or an antibody to SEQ ID NO: 2, preferably SEQ ID NO: 1.

In a sixth aspect, the problem underlying the present invention is solved by a method comprising the step immobilizing on a diagnostically useful carrier a means for specifically capturing an antibody to SEQ ID NO: 1 and/or a means for specifically capturing an antibody to SEQ ID NO: 2, preferably a means for specifically capturing an antibody to SEQ ID NO: 1, wherein the diagnostically useful carrier is preferably selected from the group comprising a bead, preferably a paramagnetic bead, a test strip, a microtiter plate, a membrane, preferably from the group comprising western blot, line blot and dot blot, a lateral flow device, a glass surface, a slide, a microarray and a biochip.

In a seventh aspect, the problem underlying the present invention is solved by a use of a polypeptide comprising SEQ ID NO: 1 and/or a SEQ ID NO: 2 or a variant thereof for the diagnosis of a Flavivirus, preferably POWV infection or for the manufacture of a kit for the diagnosis of a Flavivirus, preferably POWV infection, wherein preferably a POWV infection is distinguished from an infection with a Flavivirus other than POWV.

In a preferred embodiment the antibody to SEQ ID NO: 2 is an IgG or IgM, preferably IgG class antibody.

In a preferred embodiment, the antibody to SEQ ID NO: 1 is an IgM class antibody.

In an eighth aspect, the problem underlying the present invention is solved by a use of an IgM antibody to SEQ ID NO: 1 or a means for specifically capturing an IgM class antibody to SEQ ID NO: 1 for increasing the diagnostic reliability, preferably specificity of an immunoassay for the diagnosis of a virus, preferably Flavivirus, more preferably POWV infection.

The sample comprises antibodies from the patient, including the antibodies from the antibody classes to be detected, for example IgM or IgG class antibodies. Preferably it comprises a representative set of the entirety of the patient's antibodies. In another preferred embodiment, the antibodies from the class of antibodies to be detected are enriched, more preferably isolated. In a preferred embodiment, the sample is a blood, preferably plasma or serum or CSF sample, preferably a serum sample.

BRIEF DESCRIPTION OF THE SEVERAL VIEWS OF THE DRAWINGS

FIG. 1 shows SDS-PAGE and Coomassie staining of 1 μg purified recombinant GpE. 1 μg protein was separated on an 8-16% denaturing iD-PAGE gel, documenting high protein purity. Molecular weight markers are indicated on the left.

FIG. 2 shows SDS-PAGE and Coomassie staining of 1 μg purified recombinant NS1. 1 μg protein was separated on an 8-16% denaturing iD-PAGE gel, documenting high protein purity. Molecular weight markers are indicated on the left.

DETAILED DESCRIPTION OF THE INVENTION

Figure 3:
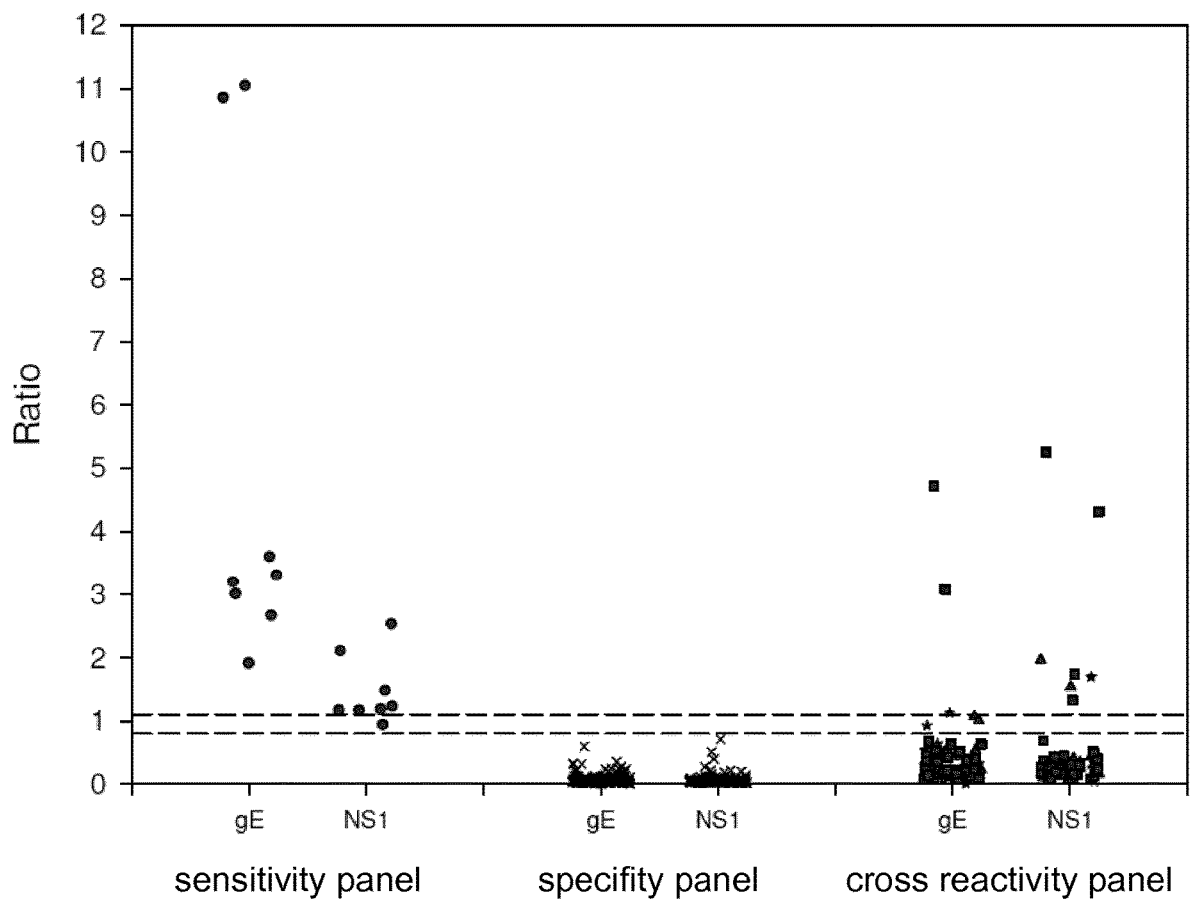
FIG. 3 shows the results of an ELISA-based assay for the detection of POWV glycoprotein E and NS1 IgM. Anti-POWV positive samples (•), samples from healthy blood donors (x), Anti-DENV positive samples (▲), Anti-WNV positive samples (★) and Anti-ZIKV positive samples (■) were included. The broken line defines a borderline range (Ratio 0.8-1.1).

The present invention is based on the inventors' surprising finding that antibodies to SEQ ID NO: 1 and/or NS1 may be used for the sensitive and specific diagnosis of an infection, preferably with POWV. Moreover, the invention is based on the inventors' surprising finding that the presence of class IgM antibodies to SEQ ID NO: 1 is a significantly more sensitive and specific indicator of infection than antibodies to GpE homologues of other Flaviviruses.

According to the present invention, the polypeptide may be a recombinant protein, wherein the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides (for example Handbooks "Strategies for Protein Purification", "Antibody Purification", published by GE Healthcare Life Sciences, and in Burgess, R. R., Deutscher, M. P. (2009): Guide to Protein Purification).

In a preferred embodiment, the polypeptide is POWV GpE, which has or comprises SEQ ID NO: 1 or A0A166AJ81 (Uniprot), preferably SEQ ID NO: 1. As throughout this application, any data base code used refers to the sequence available from said data base on the first priority date relating to said application. In another embodiment, POWV NS1 polypeptide may be used, which has or comprises SEQ ID NO: 2 or 29, preferably SEQ ID NO: 2 from the present application. In another preferred embodiment, the polypeptide according to the present invention and used for the various embodiments of the present invention is an isolated polypeptide, wherein the term "isolated", as used herein, means that the polypeptide has been enriched compared to its state upon production using a biotechnological or synthetic approach and is preferably pure, i.e. at least 10, 20, 30, 40, 50, 60, 70, 80, 90, 95 or 99 percent of the polypeptide in the respective sample consists of said polypeptide as judged by SDS polyacrylamide gel electrophoresis followed by Coomassie blue staining and quantitative determination using a computer-aided densitometer.

In a preferred embodiment, the term "variant", as used herein, may refer to at least one fragment of the full length sequence referred to, for example SEQ ID NO: 1 or SEQ ID NO: 2, more preferably SEQ ID NO: 1, more specifically one or more amino acid or nucleic acid sequence which is, relative to the full-length sequence, truncated at one or both termini by one or more amino acids. Such a fragment comprises or encodes for a peptide having at least 10, 13, 15, 25, 50, 75, 100, 150, 200, 250 or 300 successive amino acids of the original sequence or a variant thereof. The total length of the variant may be at least 13, 25, 30, 40, 50, 60, 70, 80, 90, 100 or more amino acids.

In another preferred embodiment, the term "variant" relates not only to at least one fragment, but also a polypeptide or a fragment thereof comprising amino acid sequences, preferably a fragment comprising at least 25, more preferably 50, more preferably 200, more preferably 300, more preferably 350 successive amino acids, that are at least 40, 50, 60, 70, 75, 80, 85, 90, 92, 94, 95, 96, 97, 98 99, 99.4, 99.5, 99.6, 99.7, 99.8 or 99.9% identical to the reference amino acid sequence referred to or the fragment thereof, wherein amino acids other than those essential for the biological activity, for example the ability to bind specifically to an antibody of interest, or the fold or structure of the polypeptide are deleted or substituted and/or one or more such essential amino acids are replaced in a conservative manner and/or amino acids are added or deleted such that the biological activity of the polypeptide is at least partially preserved. Known methods comprise various methods that may be used to align two given nucleic acid or amino acid sequences and to calculate the degree of identity, see for example Arthur Lesk (2008), Introduction to bioinformatics, Oxford University Press, 2008, 3$^{rd}$ edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007): Clustal W and Clustal X version 2.0. Bioinformatics, 23, 2947-2948) is used applying default settings. Exemplary variants of SEQ ID NO: 1 include the peptides EDLALPWKHKDNQD (SEQ ID NO: 5), DLALPWKHKDNQ (SEQ ID NO: 6), LALPWKHKDNQD (SEQ ID NO: 7), ALPWKHKDNQDW (SEQ ID NO: 8), LPWKHKDNQDWN (SEQ ID NO: 9) and PWKHKDNQDWNS (SEQ ID NO: 10), which bind to IgM and IgG antibodies to SEQ ID NO: 1.

In a preferred embodiment, variants may, in addition, comprise chemical modifications, for example isotopic labels or covalent modifications such as glycosylation, phosphorylation, acetylation, decarboxylation, citrullination, hydroxylation and the like. The person skilled in the art is familiar with methods for the modification of polypeptides. Moreover, variants may also be generated by way of fusion with other known polypeptides or other variants.

The variant of the polypeptide has biological activity. In a preferred embodiment, such biological activity is the ability to bind to, preferably capture specifically the respective antibody if the variant is a variant of a sequence from the group comprising SEQ ID NO: 1, or SEQ ID NO: 2, preferably SEQ ID NO: 1. For example, a variant of SEQ ID NO: 1 has the ability to capture specifically an antibody to SEQ ID NO: 1 in a sample obtained from a subject suffering from or suspected of suffering from a viral infection, preferably POWV infection. Such variants have at least one epitope recognized by the antibody to be captured, for example one epitope in SEQ ID NO: 1 if an antibody to SEQ ID NO: 1 is captured. A variant of SEQ ID NO: 2 has the ability to capture specifically an antibody to SEQ ID NO: 2 in a sample from a subject suffering from or suspected of suffering from a viral infection, preferably POWV infection.

The person skilled in the art is capable of designing variants by starting from the original SEQ ID NO: 1 sequence, introducing modifications such as point mutations, truncations and the like and subsequently confirming that the variant still has biological activity by testing whether said variant binds to an antibody to SEQ ID NO: 1 in a sample obtained from a subject suffering from the disease to be diagnosed, preferably an infection, more preferably a viral infection, more preferably an infection with a Flavivirus, most preferably an infection with POWV. The 3D protein structure of homologues of SEQ ID NO: 1 or SEQ ID NO: 2 have been published and may be used for guidance in the design of variants and choice of the sequences that may be varied without compromising the biological activity and to distinguish them from important epitopes (for example Xu et al., Contribution of intertwined loop to membrane association revealed by Zika virus full-length NS1 structure (EMBO J., published on Aug. 30, 2016, open access; Akey et al., Flavivirus NS1 structures reveal surfaces for associations with membranes and the immune system, Science 21; 343(6173):881-5. doi: 10.1126/science; WO2015/095735). Variants may be identified by identifying naturally occurring fragments derived from the full-length protein or a precursor thereof, for example by purifying them using a polypeptide comprising SEQ ID NO: 1 or SEQ ID NO: 2, preferably SEQ ID NO: 1, as an affinity ligand followed by N-terminal Edman sequencing and/or tryptic digest in combination with mass spectrometry, and using them to practice the invention. Conservative amino acid substitutions may be used for all variants.

Within the scope of the present invention is a diagnostically useful carrier comprising a means for specifically capturing an antibody to an antigen such as SEQ ID NO: 1 or SEQ ID NO: 2, preferably SEQ ID NO: 1. In a preferred embodiment, the term "specifically capturing an antibody", as used herein, refers to the ability to bind specifically to the antibody of interest, preferably an IgA, IgM or IgG class antibody, to the effect that it is bound and may be removed from the sample, whereas other antibodies, preferably from the same class and/or to another antigen, are essentially not bound and remain in the sample. The antibody is preferably an antibody that binds to the antigen of interest only such as the one represented by SEQ ID NO: 1 or SEQ ID NO: 2, preferably SEQ ID NO: 1.

The diagnostically useful carrier according to the invention serves as a scaffold for the one or more means for specifically capturing an antibody, preferably a diagnostically relevant antibody to a Flavivirus antigen such as the one represented by SEQ ID NO: 1. Said carrier is suitable for carrying out a diagnostic method. By using a carrier rather than free, soluble means for specifically capturing an antibody, it is more straightforward to isolate and separate from the sample a complex comprising the means and the antibody and to wash said complex, for example for the purpose of removing any molecules binding non-specifically to the means, complex or carrier. In a preferred embodiment, the diagnostically useful carrier is a diagnostic device, preferably selected from the group comprising a bead, preferably a paramagnetic bead, a test strip, a microtiter plate, a microarray, a blot and a membrane, and is preferably a line blot or microtiter plate, more preferably a microtiter plate. The carrier may comprise one or more controls, preferably all from the group comprising an IgM conjugate control, which confirms that a secondary antibody recognizing human IgM has been added, an IgG conjugate control, which confirms that a secondary antibody recognizing human IgG has been added, an IgA conjugate control, which confirms that a secondary antibody recognizing human IgA has been added, a serum control, which confirms that serum has been added, a negative control, which shows that there is no false positive signal, a positive control, which shows that there is no false negative signal, and one or more calibrator controls, which are preferably weak positive spots that allow for a semi-quantitative determination. If the carrier comprises several antigens, the carrier may comprise a separation band, which may indicate the spatial separation of bands, for example the control bands on one hand and the antigen bands on the other. Moreover, the carrier may comprise a cut-off band or solution, which may indicate the minimum signal for a positive result. Moreover, the carrier may comprise a coloring control, which may indicate that a coloring solution required for showing the presence of a detectable label, has been added.

The diagnostically useful carrier may be a slide, preferably glass or plastic slide for microscopy, comprising one or more eukaryotic cells, each spatially separated from each other and each expressing a polypeptide that is a means for specifically capturing an antibody. The one or more eukaryotic cells may be live cells, but are preferably fixed cells. State of the art protocols are available for fixing cells, for example using methanol or formaldehyde. Indirect immunofluorescence may be used to detect an antibody captured using such a carrier. One cell may comprise POWV GpE or a variant thereof. A cell may comprise POWV NS1 or a variant thereof. In addition, a cell may comprise a GpE protein from a Flavivirus other than POWV. In addition, a cell may comprise a GpE protein from a Flavivirus other than POWV. The cells may be arranged and the slide configured such that one drop of sample added is exposed to two or more cells at the same time, with barriers preventing cross-contamination in subsequent washing and developing reactions. The cells may be arranged and the carrier configured such that two or more cells may be examined simultaneously under a microscope.

The diagnostically useful carrier may be a bead configured for an immunoassay comprising a polypeptide comprising SEQ ID NO: 1 or a variant thereof. In a more preferred embodiment, the bead is a solid bead comprising carbohydrate such as Sepharose or synthetic polymer such as latex, preferably a paramagnetic bead, which may be removed from a solution and concentrated, preferably at the surface of a vessel, by applying a magnetic field. The bead comprises a means for capturing an antibody linked to the bead by a covalent or non-covalent bond. A mixture of beads, for example one of which linked to SEQ ID NO: 1 or a variant thereof, and/or one linked to SEQ ID NO: 2 or a variant thereof, may be used.

In a preferred embodiment, the diagnostically useful device is a microtiter plate comprising a range of wells configured for an immunoassay such as an ELISA assay. Preferably the microtiter plate comprises a well coated with a means for specifically capturing an antibody to SEQ ID NO: 1 and or SEQ ID NO: 2, preferably SEQ ID NO: 1, which means is preferably a polypeptide comprising SEQ ID NO: 1 and or SEQ ID NO: 2 or a variant thereof. In a preferred embodiment, the term "microtiter plate" is a diagnostic device, preferably made from glass or plastic, more preferably plastic, comprising one or more, preferably more than one, more preferably at least 8 wells, in which reactions in liquid buffer may be run separately without cross-contamination. At least one of the wells is coated with a polypeptide, preferably an antigenic polypeptide that may be used to specifically capture a diagnostically useful antibody. If more than one means for specifically detecting an antigen is used, then preferably each means is in a well separate from other means. The microtiter plate may be used for running several samples in parallel, preferably in an automated fashion. The wells are preferably compatible with at least one routine detection techniques such colorimetry, immunofluorescence, detection of enzymatic activity, chemiluminescence, radioactivity or the like. In addition, a separate well may include one or more antigens for detecting another Flavivirus infection and may preferably comprise a means for capturing an antibody to a GpE from a Flavivirus other than POWV. A separate well may comprise a means for capturing an antibody to a NS1 from a Flavivirus other than POWV. A separate well comprise a Flavivirus other than POWV.

In a preferred embodiment, the term "specifically detecting a captured antibody", as used herein, means that the antibody binding specifically to the means for specifically capturing the antibody, preferably a polypeptide comprising SEQ ID NO: 1 or SED ID NO: 2, preferably SEQ ID NO: 1 or a variant thereof, following capture, binds specifically to the means for detecting the antibody, for example a secondary antibody. In a preferred embodiment, the term "specifically capturing an antibody", as used herein, means that the means for specifically capturing an antibody binds specifically to the antibody and does not bind, at a significant or detectable level to any other antibody. In a preferred embodiment, the term "binding specifically", as used herein, means that the binding is stronger than a binding reaction characterized by a dissociation constant of $1 \times 10^{-5}$ M, more preferably $1 \times 10^{-7}$ M, more preferably $1 \times 10^{-8}$ M, more preferably $1 \times 10^{-9}$ M, more preferably $1 \times 10^{-10}$ M, more preferably $1 \times 10^{-11}$ M, more preferably $1 \times 10^{-12}$ M, as determined by surface plasmon resonance using Biacore equipment at 25° C. in PBS buffer at pH 7.

In a preferred embodiment, the term "specifically detecting of an antibody", which antibody belongs to a certain class of antibodies, for example IgA, IgM or IgG class antibodies, means that said antibody is detected in an assay spatially separated from any binding reaction involving the detection of antibodies to the same antigen associated with another class and, more preferably, no antibody from another class against the same antigen is detected in the same reaction, for example an ELISA well. In other words, the assay is carried out such that the readout allows to distinguish between antibody classes, for example IgG or IgM antibodies from other antibody classes, and to conclude and detect specifically to which antibody class the detected antibody belongs or to detect only a specific class of antibody to an antigen of interest, preferably IgM antibodies to SEQ ID NO: 1 or IgG antibodies to SEQ ID NO: 2. This does not rule out that antibodies to the same antigen, but associated with another class of antibodies, may be detected in a spatially separate reaction simultaneously. For example, binding reactions involving the same antigen such as SEQ ID NO: 1 or SEQ ID NO: 2 or a variant thereof, may be run in separate wells of an ELISA microtiter plate, but may be developed using secondary antibodies binding to different classes of antibodies, for example IgM and IgG, respectively.

In a preferred embodiment, an antibody from one Ig class only is detected, preferably from the group comprising IgG, IgM and IgA, preferably IgM. This means more preferably that antibodies from any other class binding to the same antigen as the antibody to be detected are not detected in the same reaction vessel, so that the binding of the antibody from one Ig class can be distinguished from the binding of an antibody from another Ig class. For example, if an IgM antibody is detected, IgG or IgA antibodies binding to the same means for capturing an antibody will not be detected. This does not exclude that the other Ig class antibody, preferably IgG and/or IgA is detected simultaneously in a spatially separate reaction. For example, two separate vessels such as wells in a microtiter plate may comprise the same means for specifically capturing the antibody, but the antibody captured may be detected using two different means for specifically detecting, for example secondary antibodies, for example a secondary antibody for specifically detecting an IgG class antibody and a secondary antibody for detecting an IgM class antibody.

In a preferred embodiment, an IgM class antibody to PWV GpE is detected. In a preferred embodiment, an IgG class antibody to PWV GpE is detected. In a preferred embodiment, an IgA class antibody to PWV GpE is detected. In a preferred embodiment, an IgM class antibody to PWV NS1 is detected. In a preferred embodiment, an IgG class antibody to PWV NS1 is detected. In a preferred embodiment, an IgA class antibody to PWV NS1 is detected. In a more preferred embodiment, an IgM antibody to GpE from a flavivirus other than PWV is detected in addition. In a more preferred embodiment, an IgG antibody to GpE from a flavivirus other than PWV is detected in addition. In a more preferred embodiment, an IgA antibody to GpE from a flavivirus other than PWV is detected in addition. In a more preferred embodiment, an IgM antibody to NS1 from a flavivirus other than PWV is detected in addition. In a more preferred embodiment, an IgG antibody to NS1 from a flavivirus other than PWV is detected in addition. In a more preferred embodiment, an IgA antibody to NS1 from a flavivirus other than PWV is detected in addition.

According to the present invention, a means for specifically detecting a captured antibody is provided or used to practice the present invention, optionally as part of a kit. In a preferred embodiment, the term "a means for specifically detecting a captured antibody", as used herein, refers to a reagent that binds specifically to the captured antibody, preferably to its constant region, such that the antibody captured or to be captured remains capable of binding to its antigen. The sequence of the constant region depends on the organism from which the sample is taken and analyzed, and the antibody class. Preferably, the means binds to human IgA, IgM or IgG class antibodies. If an antibody to SEQ ID NO: 1 is detected, it is preferred that the secondary antibody recognizes the constant region of IgM class antibodies. If an antibody to SEQ ID NO: 2 is detected, it is preferred that the secondary antibody recognizes constant region of IgG class antibodies.

In a more preferred embodiment, the means for specifically detecting a captured antibody is selected from the group comprising a secondary antibody, an aptamer and an anticalin (Skerra, A. (2008). "Alternative binding proteins: anticalins—harnessing the structural plasticity of the lipocalin ligand pocket to engineer novel binding activities". FEBS J. 275 (11): 2677-83) and is most preferably a secondary antibody. A secondary antibody may be a mammalian antibody, more preferably selected from the group comprising a cow, goat, chicken, rat, murine, porcine, equine or rabbit antibody. The means may comprise a detectable label, preferably from the group comprising an enzymatically active, colored label, preferably from the group comprising a gold and a latex label, chemiluminescent and fluorescent label.

If a polypeptide is used as the means for specifically capturing an antibody, said polypeptide, preferably comprising one or more sequences selected from the group comprising SEQ ID NO: 1 or SEQ ID NO: 2, preferably SEQ ID NO: 1, when used to carry out the teachings of the present invention, may be provided in any form and at any degree of purification, from tissues or cells comprising said polypeptide in an endogenous form, more preferably cells overexpressing the polypeptide, crude or enriched lysates of such cells, to purified and/or isolated polypeptide which may be essentially pure. In a preferred embodiment, the term "overexpressing", as used herein, means that the cell, preferably a eukaryotic, more preferably a mammalian or insect, more preferably a mammalian, more preferably a human cell, most preferably a HEK293 or HEK293T cell, has been genetically engineered such that it expresses more of the protein of interest than a non-engineered wild type cell would. In a preferred embodiment, the polypeptide is a native polypeptide, wherein the term "native polypeptide", as used herein, refers to a folded polypeptide comprising at least 15, 30, 50, 100 150, 200, 300 or 350 amino acids, preferably more than 30 amino acids, more preferably to a folded polypeptide purified from tissues or cells, more preferably from mammalian cells or tissues, optionally from non-recombinant tissues or cell. In another preferred embodiment, the polypeptide is a linear peptide having at least 7, more preferably at least 10 amino acid residues. If a native polypeptide is used, it is preferably enriched compared to its natural state. A recombinant polypeptide may comprise a C-terminal or N-terminal tag for affinity purification, immobilization or detection such as a His tag, as exemplified by SEQ ID NO: 3 or SEQ ID NO: 4, or a streptavidin tag, preferably a streptavidin, which tag may preferably be removed by cleavage using a protease recognizing a protease cleavage site in a polypeptide linker between the tag and the N terminus or C-terminus, respectively, as part of the purification or method. The cleaved polypeptide may subsequently be attached to a diagnostically useful carrier to yield the diagnostically useful carrier according to the present invention. In another preferred embodiment, the means for specifically capturing an antibody is a POWV-infected eukaryotic, preferably human cell. Such a cell may be evaluated by fluorescence microscopy. The cells may be transiently or stably transfected, preferably transiently transfected, preferably with a vector comprising a sequence encoding SEQ ID NO: 1 or SEQ ID NO: 2, preferably SEQ ID NO: 2, under the control of an inducible or constantly induced promotor.

Said means for specifically capturing an antibody, together with the insoluble carrier to which it is attached, may be separated from a sample from a subject in a straightforward manner, for example by filtration, centrifugation, magnetism or decanting. Said means may be immobilized in a reversible or irreversible manner. For example, the immobilization is reversible if the means interacts with the carrier via ionic interactions which may be masked by addition of a high concentration of salt or if the molecule is bound via a cleavable covalent bond or a noncovalent bond. By contrast, the immobilization is irreversible if the means is tethered to the carrier via a covalent bond that cannot be cleaved in aqueous solution. The means may be indirectly immobilized, for example by immobilizing an antibody or other entity having affinity to the polypeptide, followed by addition of the means and formation of a means-antibody complex. A non-covalent bond may be made by chemically attaching a ligand to the carrier, preferably via a covalent bond, and fusing to the means a polypeptide having affinity to the ligand. In a preferred embodiment, the ligand is selected from the group comprising biotin, in which case the polypeptide having affinity may be streptavidin or a variant thereof binding to biotin, glutathione (polypeptide having affinity: glutathione-S-transferase), Nickel (polypeptide having affinity: His tag), Flag tag (polypeptide having affinity: anti-flag antibody), carbohydrate such as maltose or cellulose (polypeptide having affinity: maltose or cellulose binding protein), and is preferably biotin.

According to the present invention, a nucleic acid encoding the polypeptide according to the present invention such as a polypeptide comprising SEQ ID NO: 1 or SEQ ID NO: 2, preferably SEQ ID NO: 1 or a variant thereof, optionally with an inducible promotor, which polypeptide is preferably for use for the diagnosis of a disease or the manufacture of a kit or reagent for such use, is provided. Said nucleic acid may be a part of a vector, preferably for expressing said nucleic acid. A eukaryotic or prokaryotic, preferably eukaryotic cell comprising this vector and preferably expressing the polypeptide encoding by the vector, is also provided. The nucleic acid, the vector and the cell may be used for the manufacture of a kit for use according to the present invention such as use of an antibody to SEQ ID NO: 1 or SEQ ID NO: 2, preferably SEQ ID NO: 1. The nucleic acid may be expressed, the polypeptide encoded purified and used, preferably immobilized on a diagnostically useful carrier, in order to make the diagnostically useful carrier according to the present invention. The nucleic acid may be used to design and prepare a nucleic acid construct encoding a variant of the polypeptide for expression and use of the resulting variant for the preparation of a diagnostically useful carrier and for the detection of the respective antibody such as an antibody to SEQ ID NO: 1 or SEQ ID NO: 2, preferably SEQ ID NO: 1.

The inventive teachings provide a kit, preferably for diagnosing an infection, more preferably for diagnosing a flavivirus infection, most preferably a POWV infection. Such a kit is a container that comprises specific reagents required to practice the inventive method, in particular the diagnostically useful carrier according to the present invention, optionally in addition to one or more reagents and solutions required to practice the inventive method, preferably selected from or all from the group comprising sample dilution buffer, washing buffer and a means for detecting any specifically captured antibody and optionally a means for detecting the specifically captured antibody, which may optionally be attached to the secondary antibody, for example a fluorescent, enzymatically active, radioactive, chemiluminescent, preferably electrochemiluminescent label or a spin label. The kit may comprise a chemical solution for carrying out a detection reaction such as 3,3', 5,5'-tetramethylbenzidine, p-Nitrophenyl Phosphate, 2,2'-Azinobis [3-ethylbenzothiazoline-6-sulfonic acid or o-phenylenediamine dihydrochloride for a colorimetric reaction tripropylamine for an electrochemiluminescence reaction. Furthermore, it may comprise instructions detailing how to use the kit and the inventive diagnostically useful carrier for contacting the inventive polypeptide with a bodily fluid sample from a subject, preferably a human subject. The kit may comprise a negative and/or a positive control serum, more preferably both. The kit may comprise a coloring or developing solution for showing the presence of a detectable label depending on this, for example an enzymatically active or chemiluminescent label, respectively.

Furthermore, the kit may comprise a positive control, for example a recombinant antibody known to bind to SEQ ID NO: 1 and/or a recombinant antibody known to bind to SEQ ID NO: 2, and a negative control, for example a protein having no detectable affinity to SEQ ID NO: 1 or to SEQ ID NO: 2. Finally, the kit may comprise one or more calibrators, which is preferably a solution comprising a SEQ ID NO: 1-binding and/or SEQ ID NO: 2-binding, preferably SEQ ID NO: 1-binding antibody for preparing a calibration curve. In a more preferred embodiment, the kit comprises more than one, preferably three or more calibrators comprising different concentrations of an antibody to SEQ ID NO: 1, which antibody is preferably recognized by a secondary antibody to human IgM class antibodies. In a more preferred embodiment, the kit comprises at least one antibody to SEQ ID NO: 2, which antibody is preferably recognized by a secondary antibody to human IgG class antibodies. Such calibrator may be or comprise a chimeric antibody comprising a human constant region and optionally a variable region from a mammal other than a human. If more than one calibrator is used, the two or more calibrators comprise different concentrations of the antibody, preferably at a range of concentrations that allow the user to set up a calibration curve.

If IgM class antibodies binding to SEQ ID NO: 1 or SEQ ID NO: 2, preferably SEQ ID NO: 1 are detected, IgG class antibodies may be removed or their concentration may be decreased prior to determining the IgM class antibodies. This may be achieved by pre-absorbing IgG class antibodies, for example by contacting them with an anti-IgG antibody, for example a mammalian, preferably goat anti-human IgG antibody. This antibody may absorb IgG antibodies that may interfere with the IgM detection assay. Suitable reagents are commercially available, for example EUROSORB commercialized by EUROIMMUN, Lubeck. Alternatively, this may be achieved by isolating the entirety of IgM class antibody prior to detecting an IgM antibody to SEQ ID NO: 1 or SEQ ID NO: 2, preferably SEQ ID NO: 1.

For therapeutic purposes, a vaccine may be provided that comprises the polypeptide comprising SEQ ID NO: 1 and/or the polypeptide comprising SEQ ID NO: 2, preferably SEQ ID NO: 1 or a variant thereof may be formulated with one or more diluents, one or more glidants, and/or one or more filling agents. The preparation of suitable formulations is described in the state of the art, for example in US20130022631A1. The vaccine formulation may comprise, in addition to the purified polypeptide, a pharmaceutically accepted buffer such as phosphate or phosphate-citrate buffer in the pH range 6.4-7.5 with added stabilizing agents that may include one or more of the following, but is not limited to: human serum albumin, gelatin, reducing and non-reducing sugars, amino acids, polyols such as sorbitol and mannitol, glycerol organic and inorganic salts, polyvinyl pyrrolidone etc. The stable formulation may be in a liquid form is suitable for intramuscular/intradermal/subcutaneous/intravenous administration in a human host. The stable formulation may be in a dry lyophilized form can be reconstituted with a suitable solvent before administration. The formulations may be suitable for oral and intranasal administration in humans.

The invention provides a pharmaceutical composition or a vaccine, which composition or immunogenic composition such as a vaccine comprises a polypeptide comprising SEQ ID NO: 1 and/or SEQ ID NO: 2, preferably SEQ ID NO: 1 or a variant thereof An immunogenic composition or vaccine may comprise components to inactivate a virus or bacteria and stabilize the vaccine, helping to preserve the vaccine and prevent it from losing its potency over time. Adjuvants are added to vaccines to simulate the production of antibodies against the vaccine to make it more effective. An adjuvant could be organic or inorganic. The most common inorganic adjuvants for human vaccines include aluminum phosphate and aluminum hydroxide. Organic adjuvants could be based on the organic compound squalene and an oil [squalene] in water adjuvant can be used.

An immunogenic composition may comprise stabilizers that help the vaccine to maintain its effectiveness during storage, e.g., $MgCl_2$, $MgSO_4$, lactose-sorbitol, or sorbitol-gelatin, and preservatives to prevent bacterial and fungal growth, e.g., thiomersal, formaldehyde, or phenol derivatives, antibiotics. The composition is preferably suitable for administration to a subject, preferably a mammalian subject, more preferably to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parentally", as used herein, comprises subcutaneous, intracutaneous, intravenous, intramuscular, intra-articular, intrasynovial, instrasternal, intrathecal, intralesional and intracranial injection or infusion techniques. The pharmaceutical composition may be provided in suitable dosage forms, for example capsules, tablets and aqueous suspensions and solutions, preferably in sterile form. It may be used in a method of treatment of a disease, which method comprises administering an effective amount of the inventive polypeptide to a subject.

The inventive method for diagnosing a Flavivirus infection, preferably for distinguishing a primary from a secondary Flavivirus infection, may comprise the step detecting in a first sample from a subject an IgA class antibody to NS1 of a Flavivirus, preferably POWV, optionally further comprising detecting in said first sample an IgM and/or IgG class, preferably IgM class antibody to NS1 of a Flavivirus, preferably POWV, such as SEQ ID NO: 2 or a variant thereof. In a preferred embodiment, the method further comprises the step detecting in a second sample obtained from said subject an IgA class antibody to NS1 of said Flavivirus, optionally further comprising detecting in said second sample an IgM and/or IgG class, preferably IgM class antibody to NS1 of a Flavivirus such as SEQ ID NO: 2, optionally further comprising detecting in said first sample an IgM and/or IgG class, preferably IgM class antibody to NS1 of a Flavivirus, more preferably SEQ ID NO: 2.

A dynamic titer of IgA or IgM, preferably IgA class antibodies to NS1 of a Flavivirus, preferably to SEQ ID NO: 2, increasing and decreasing significantly relatively to the background before emergence of IgG class antibodies (i.e. seroconversion), may indicate an acute POWV infection, which is a primary Flavivirus infection. By contrast, a parallel increase of IgA and IgG (albeit the latter at higher levels) may indicate an acute POWV infection, which is a secondary Flavivirus infection. In a preferred embodiment, the first sample is obtained at least 3, 4, 5, 6 days, 1, 2 3 or 4 weeks following the subject's exposure or suspected exposure to a Flavivirus. In a preferred embodiment, the first sample is taken in the two weeks after onset of symptoms. The presence or absence of antibodies may be determined as well as their relative levels over time. The second sample may be obtained at least 3, 4, 5, 6 days, 1, 2, 4, 6, 8, 12, 16, 20, 24, 28 or 32 weeks later than the first sample, preferably at least 3 days, more preferably at least 7 days. A total number of at least 2, 3, 4, 5 or six samples may be taken, preferably at least 2 samples, optionally each sample at least 1 day, 3 days, one week, preferably one week after the previous sample. The total concentrations of IgG, IgM and/or IgA, preferably IgM, may be determined in addition, for example to rule out insufficiencies. This way, the titers of the respective antibodies may be monitored over time.

In a preferred embodiment, the titer of IgM, IgG and/or IgA, preferably IgA and IgG, more preferably IgA to NS1, preferably to SEQ ID NO: 2 is monitored by detecting the presence or absence or, preferably relative level over time for a period of at least 3, 4, 5, 6, 10, 14, 21, 28, 35 or 42 days, preferably at least 6 days, with the first sample being taken at least five days, preferably at least 7 days following onset of the symptoms. Seroconversion may be detected by monitoring the presence or absence or relative level over time of IgG class antibodies to NS1, preferably SEQ ID NO: 2. This may help identify the time window in which the increase and decrease of IgM and/or IgA class antibodies would be expected or concluding that this time window has passed.

The inventive method, kit and carriers may be used to distinguish between a primary and a secondary Flavivirus infection, preferably POWV infection. In a preferred embodiment, the term "primary infection", as used herein, refers to an infection of a person who has never had an infection with said Flavivirus or another Flavivirus, preferably said Flavivirus, more preferably the POWV, by contrast to a secondary infection in a patient who has been exposed to a virus or immunogenic compositions derived thereof before. In a preferred embodiment, this may involve distinguishing a primary POWV infection from a secondary infection with another Flavivirus.

A Flavivirus other than POWV may be selected from the group comprising dengue virus 1, dengue virus 2, dengue virus 3, dengue virus 4, Yellow fever virus, Tick-borne encephalitis virus, Usutu virus, West Nile virus, Zika virus and Japanese encephalitis virus, or may refer to two or more viruses from this group, preferably all of them.

In addition, the presence of an antibody to an NS1 from a Flavivirus other than POWV may be detected or the diagnostically useful carrier may comprise a means for capturing an antibody to an NS1 from a Flavivirus other than POWV. An NS1 protein from a Flavivirus other than POWV may comprise all or may be selected from the group comprising Zika NS1 (SEQ ID NO: 11), dengue virus 1 NS1 (SEQ ID NO: 12), dengue virus 2 NS1 (SEQ ID NO: 13), dengue virus 3 NS1 (SEQ ID NO: 14), dengue virus 4 NS1 (SEQ ID NO: 15), West Nile virus NS1 (SEQ ID NO: 6 from WO2017/144174), Tick-borne encephalitis virus NS1 (SEQ ID NO: 17), Japanese encephalitis virus NS1 (SEQ ID NO: 18) and Yellow fever virus NS1 (SEQ ID NO: 19) or a variant thereof.

In addition, the presence of an antibody to a GpE from a Flavivirus other than POWV may be detected or the diagnostically useful carrier may comprise a means for capturing an antibody to an NS1 from a Flavivirus other than POWV. A GpE protein from a Flavivirus other than POWV may comprise all or may be selected from the group comprising Zika GpE (SEQ ID NO: 20), dengue virus 1 GpE (SEQ ID NO: 21), dengue virus 2 GpE (SEQ ID NO: 22), dengue virus 3 GpE (SEQ ID NO: 23), dengue virus 4 GpE (SEQ ID NO: 24), West Nile virus GpE (SEQ ID NO: 25). Tick-borne encephalitis virus GpE (SEQ ID NO: 26), Japanese encephalitis virus GpE (SEQ ID NO: 27) and Yellow fever virus GpE (SEQ ID NO: 28) or a variant thereof.

In addition, the presence of an antibody to a GpE from a Flavivirus other than POWV may be detected or the diagnostically useful carrier may comprise a means for capturing an antibody to a GpE from a Flavivirus other than POWV. An GpE protein from a Flavivirus other than POWV may be selected from the group comprising Zika GpE (SEQ ID NO: 20), dengue virus 1 GpE (SEQ ID NO: 21), dengue virus 2 GpE (SEQ ID NO: 22), dengue virus 3 GpE (SEQ ID NO: 23), dengue virus 4 GpE (SEQ ID NO: 24) West Nile virus GpE (SEQ ID NO: 25), Tick-borne encephalitis virus GpE (SEQ ID NO: 26), Japanese encephalitis virus GpE (SEQ ID NO: 27) and Yellow fever virus GpE (Uniprot Q6DV88) or a variant thereof.

In many cases detecting or detecting the presence of an antibody, optionally meaning determining whether the concentration of the antibody is beyond a certain threshold preferably as set by measurement using ELISA, preferably as described in Example 1, in the implicit detection limit by this method, often suggested by the detection limit, in the sample, is sufficient for the diagnosis. If the antibody can be detected, this will be information instrumental for the clinician's diagnosis and indicates an increased likelihood that the patient suffers from a disease. In a preferred embodiment, the relative concentration of the antibody in the serum, compared to the level that may be found in the average healthy subject, may be determined. In a preferred embodiment, the term "detecting the presence", as used herein, means that it is sufficient to check whether a signal sufficiently beyond any background level may be detected using a suitable complex detection method that indicates that the antibody of interest is present or more antibody of interest is present than would be in a healthy subject. In a more preferred embodiment this may involve determining whether the concentration is at least 0.1, preferably 0.2, 0.5, 1, 2, 5, 10, 20, 25, 50, 100, 200, 500, 1000, 10000 or 100000 times higher than the concentration of the antibody of interest found in the average healthy subject.

In a preferred embodiment, the term "diagnosis", as used herein, refers to any kind of procedure aiming to obtain information instrumental in the assessment whether a patient suffers or is likely or more likely than the average or a comparative subject, the latter preferably having similar symptoms, to suffer from a certain disease or disorder in the past, at the time of the diagnosis or in the future, to find out how the disease is progressing or is likely to progress in the future or to evaluate the responsiveness of a patient with regard to a certain treatment, for example the administration of suitable drugs such as drugs for the desensitization of allergic patients. In other words, the term "diagnosis" comprises not only diagnosing, but also prognosticating and/or monitoring the course of a disease or disorder.

Therefore, the term "diagnosis" does preferably not imply that the diagnostic methods or agents according to the present invention will be definitive and sufficient to finalize the diagnosis on the basis of a single test, let alone parameter, but may refer to a contribution to what is referred to as a "differential diagnosis", i.e. a systematic diagnostic procedure considering the likelihood of a range of possible conditions on the basis of a range of diagnostic parameters. The term "diagnosis" may also refer to a method or agent used to choose the most promising treatment regime for a patient. In other words, the method or agent may relate to selecting a treatment regimen for a subject.

The invention may be used to provide a prognosis whether a pregnant woman's newborn child is likely to suffer from a deformity if the sample from the pregnant woman is tested. Preferably, the pregnant woman may have symptoms suggesting that she may suffer from a flaviviral infection or may very actually suffer from an infection.

The present invention relates to a method comprising the step detecting in a sample from a subject the presence or absence of an antibody to an antigenic polypeptide such as a polypeptide comprising a SEQ ID NO: 1 or SEQ ID NO: 2, preferably SEQ ID NO: 1 or a variant thereof. This method preferably comprises immobilizing said antibody followed by specific detection of said antibody, for example by way of the steps a) (optionally) providing a sample from a subject, b) contacting the sample with the diagnostically useful carrier according to the present invention under conditions compatible with the formation of a complex comprising the diagnostically useful carrier and the antibody, more specifically the means for specifically capturing the antibody and the antibody, c) isolating any said complex, for example by removing the sample, d) optionally washing said complex, and e) optionally detecting said complex. The method is preferably an in vitro method. The detection of the complex for the prognosis, diagnosis, methods or test kit according to the present invention comprises the use of a method selected from the group comprising immunodiffusion techniques, immunoelectrophoretic techniques, light scattering immunoassays, agglutination techniques, labeled immunoassays such as those from the group comprising radiolabeled immunoassay, enzyme immunoassays such as colorimetric assays, chemiluminescence, preferably electrochemiluminescence, immunoassays and immunofluorescence techniques. The person skilled in the art is familiar with these methods, which are also described in the state of the art, for example in Zane, H. D. (2001): Immunology—Theoretical & Practical Concepts in Laboratory Medicine, W. B. Saunders Company, in particular in Chapter 14. The method may further involve testing the avidity of antibodies to SEQ ID NO: 1 or SEQ ID NO: 2 in the sample, preferably of antibodies to SEQ ID NO: 1.

The present invention is further illustrated by the following examples, sequences and figures from which further features, embodiments, aspects and advantages of the present invention may be taken. All methods and materials similar or equivalent to those described herein can be used in the practice or testing of the present invention, with suitable methods and materials being described herein. All publications, patent applications, patents, and other references mentioned herein are incorporated by reference in their entirety. Further, the materials, methods, and examples are illustrative only and are not intended to be limiting, unless otherwise specified.

FIG. 1 shows SDS-PAGE and Coomassie staining of 1 μg purified recombinant GpE. 1 μg protein was separated on an 8-16% denaturing iD-PAGE gel, documenting high protein purity. Molecular weight markers are indicated on the left.

FIG. 2 shows SDS-PAGE and Coomassie staining of 1 μg purified recombinant NS1. 1 μg protein was separated on an 8-16% denaturing iD-PAGE gel, documenting high protein purity. Molecular weight markers are indicated on the left.

FIG. 3 shows the results of an ELISA-based assay for the detection of POWV glycoprotein E and NS1 IgM. Anti-POWV positive samples (•), samples from healthy blood donors (x), Anti-DENV positive samples (]), Anti-WNV positive samples (★) and Anti-ZIKV positive samples (■) were included. The broken line defines a borderline range (Ratio 0.8-1.1).

Figure 4:
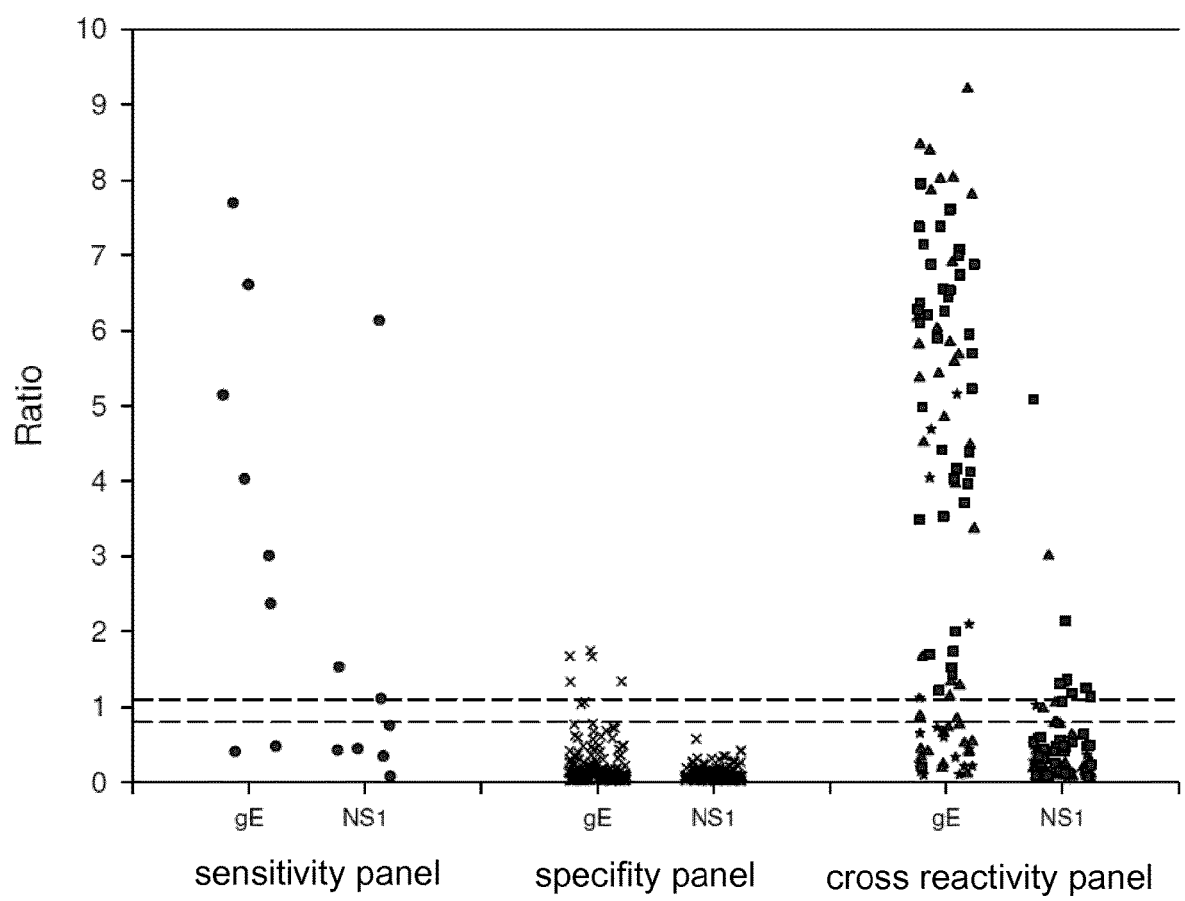
FIG. 4 shows the results of an ELISA-based assay for the detection of POWV glycoprotein E and NS1 IgG. Anti-POWV positive samples (•), samples from healthy blood donors (x), Anti-DENV positive samples (▲), Anti-WNV positive samples (★) and Anti-ZIKV positive samples (■) were included. The broken line defines a borderline range (Ratio 0.8-1.1).

FIG. 4 shows the results of an ELISA-based assay for the detection of POWV glycoprotein E and NS1 IgG. Anti-POWV positive samples (•), samples from healthy blood donors (x), Anti-DENV positive samples (▲), Anti-WNV positive samples (★) and Anti-ZIKV positive samples (■) were included. The broken line defines a borderline range (Ratio 0.8-1.1).

EXAMPLES

Example 1: POWV GpE Protein Expression and Purification

Recombinant POWV GpE was expressed in Sf9 cells using standard cloning and expression methods based on the pHEP plasmid with an artificial signal sequence and a C-terminal His tag (SEQ ID NO: 1). Transfected cells were cultures at 27.5° C. in Insect-XPRESS™ Proteinfree Insect Cell Medium with L-glutamine for four days. Cells were harvested, resuspended in 20 mM Tris-HCl pH 7.4, 10% (w/v) sucrose, 5 mM EDTA, 1 mM PMSF and stored at −80° C. until further use.

To prepare GpE, cell culture supernatant was adjusted to 11 mmol/l MOPS pH7, 0, 200 mmol/l sodium chloride, 50 mmol/l magnesium chloride, 20 mmol/l imidazole, cleared by centrifugation for 30 minutes at 17,600×g, 4° C., applied to Nickel Rapid Run (Agarose Bead Technologies, Miami, Fla., USA) equilibrated with 10 mmol/l MOPS pH 7.0, 300 mmol/l sodium chloride, 20 mmol/l imidazole and eluted by increasing the imidazole concentration to 150 mmol/l. All fractions containing GpE[POWV] were pooled and concentrated by ultrafiltration (Vivaspin, Sartorius, Gottingen, Germany). The final preparation was stored at −80° C. until further use.

The final protein preparation of GpE were treated with or without 16 mmol/l dithiothreitol and incubated at 70° C. or at room temperature for 10 minutes, followed by SDS gel electrophoresis and Coomassie staining.

When separated by SDS-PAGE, GpE migrated essentially according to its predicted molecular mass (49 kDa; FIG. 1). Protein identity was verified by mass spectrometry.

Example 2: POWV NS1 Protein Expression and Purification

Recombinant POWV NS1 was expressed in HEK293T cells using standard cloning and expression methods based on the pTriEx-1 plasmid with an artificial signal sequence and a C-terminal His tag (SEQ ID NO 2). Transfected cells were cultures at 37° C. and 8.5% CO2 in Dulbecco's modified eagle's medium with 10% fetal calf serum, 100 U/ml penicillin and 0.1 mg/ml streptomycin for three to five days. Cells were harvested, resuspended in 20 mM Tris-HCl pH 7.4, 10% (w/v) sucrose, 5 mM EDTA, 1 mM PMSF and stored at −80° C. until further use.

To prepare NS1, cell culture supernatant was adjusted to 5 mmol/l tris chloride pH 8.0, 164 mmol/l sodium chloride, 50 mmol/l magnesium chloride, 20 mmol/l imidazole, 0.1% Triton X-100, cleared by centrifugation for 30 minutes at 17,600×g, 4° C., applied to Nickel Rapid Run (Agarose Bead Technologies, Miami, Fla., USA) equilibrated with 5 mmol/l tris chloride pH 8.0, 300 mmol/l sodium chloride, 20 mmol/l imidazole and eluted by increasing the imidazole concentration to 150 mmol/l. All fractions containing NS1

[POWV] were pooled and concentrated by ultrafiltration (VivaSpin, Sartorius, Gottingen, Germany). The final preparation was stored at −80° C. until further use.

The final protein preparation of NS1 was treated with or without 16 mmol/l dithiothreitol and incubated at 70° C. or at room temperature for 10 minutes, followed by SDS gel electrophoresis and Coomassie staining.

When separated by SDS-PAGE, NS1 migrated essentially according to its predicted molecular mass (43.2 kDa; FIG. 2). Protein identity was verified by mass spectrometry.

Example 3 and 4: ELISA-Based Assay for the Detection of POWV Glycoprotein E IgM and ELISA-Based Assay for the Detection of POWV NS1 IgG The following experiments were performed to evaluate the performance of different Powassan virus antigens in an indirect ELISA for the detection of specific anti-POWV virus antibodies in human serum or plasma, more specifically PWS GpE and NS1 as prepared in Examples 1 and 2, respectively.

Samples

Panel 1 (sensitivity panel): Eight clinical samples (7 serum samples; 1 CSF sample) of patients with acute POWV infection.

Panel 2 (specificity panel): 171 samples which originate from healthy individuals. Previous exposure to POWV is highly unlikely because of the origin of the samples (Germany) and the rare occurrence of infections even in endemic regions.

Panel 3 (cross reactivity panel): This panel consists of 40 samples positive for antibodies against Dengue virus, 17 samples positive for antibodies against West Nil virus and 39 samples positive for antibodies against Zika virus. This panel will be used for determination of cross-reactivity of the antigens used.

1. Preparation of Coated Microtiter Plates:

Two different POWV antigens were used: glycoprotein E (GpE; prepared from cell culture supernatant of Sf9 cells) and non-structural protein 1 (NS1; prepared from cell culture supernatant of HEK293 cells).

For use in microtiter ELISA these antigens were diluted in PBS to final concentrations of 2.5 µg/ml, respectively. Microtiter plates were coated with 100 µl of antigen dilution per well.

2. Anti-POWV IgM ELISA:

All reagents used during this experiment are included in every EUROIMMUN IgM ELISA Test-Kit for infectious diagnostics (e.g. EI 2668-9601 M). Sera were diluted 1:101 in IgM sample buffer containing IgG/RF absorbent and incubated at room temperature for 10 min to absorb rheumatoid factors and IgG. Samples were applied to microtiter plates and incubated as described for commercial EUROIMMUN ELISA Test-Kits (e.g. EI 2668-9601 M). In brief: 60 min at 37° C.; 3 washing steps using EUROIMMUN wash buffer; addition of 100 µl of peroxidase-labelled anti-human IgM conjugate (goat) per well; incubation for 30 min at room temperature; 3 washing steps using EUROIMMUN wash buffer; addition of 100 µl of chromogen/substrate solution (TMB/H2O2) per well; incubation for 15 min at room temperature; addition of 100 µl stop-solution (0.5 M sulfuric acid); measurement of optical density at 450 nm.

Panel 1 was used for evaluation of sensitivity of the respective antigens for detection of specific anti-POWV IgM antibodies. Panel 2 and Panel 3 were incubated to determine specificity and cross reactivity of the test system.

3. Anti-POWV IgG ELISA:

All reagents used during this experiment are included in every EUROIMMUN IgG ELISA Test-Kit for infectious diagnostics (e.g. EI 2668-9601 G). Sera were diluted in IgG sample buffer and diluted samples were applied to microtiter plates and incubated as described for the anti-POWV IgM ELISA.

Panel 1 was used for evaluation of sensitivity of the respective antigens for detection of specific anti-POWV IgG antibodies. Panel 2 and Panel 3 were incubated to determine specificity and cross reactivity of the test system.

Results

1. Sensitivity and Specificity of Anti-POWV IgM ELISA

Comparison of GpE and NS1 antigens for the detection of specific anti-POWV IgM antibodies showed high sensitivity for ELISA using either of the antigens (GpE: 100.0% [8/8]; NS1: 87.5% [7/8]) (FIG. 3). Nevertheless, usage of GpE led to higher reactivity of positive samples suggesting higher sensitivity when used for screening. There were no advantages achieved by using NS1 with regard to specificity (98.2% [NS1] vs. 97.1% [GpE]) and cross reactivity (FIG. 3). In contrast, cross reactivity was lower for the GpE-based ELISA than for the NS1-based ELISA (DENV: 5.0% vs. 0.0%; WNV: 5.9% vs. 5.9%; ZIKV: 10.3% vs. 5.1%).

2. Sensitivity and Specificity of Anti-POWV IgG ELISA

Comparison of GpE and NS1 antigens showed sensitivities of 75.0% and 37.5%, respectively. The sample set used for evaluation of sensitivity of this test are samples originating from patients with acute infections. If these samples were drawn at early time points of infection there is the possibility of lacking anti-Powassan IgG because of seroconversion has not taken place yet. GpE suggests to be more sensitive for the detection of IgG, but due to higher cross reactivity of GpE in comparison to NS1 (FIG. 4), IgG antibodies measured may result from earlier flavivirus contact or vaccination (e.g. YFV vaccination).

The NS1-based anti-POWV IgG ELISA showed a specificity of 95.3% in panel 2 (healthy blood donors), in contrast to 87.9% for the GpE based ELISA. Again the lower specificity of GpE may result from prevalence of antibodies directed against other flaviviruses.

The higher specificity of the NS1-based ELISA was strengthened by drastic reduction of cross reactivity with samples positive for antibodies against Dengue virus (5.0% vs. 62.5%), Zika virus (17.9% vs. 97.4%) and West Nil virus (0.0% vs. 29.4%) (FIG. 4).

CONCLUSION

Based on the data shown above, GpE was selected for the anti-POWV IgM ELISA. This antigen allowed development of a specific test which shows highly sensitive detection of positive samples while the level of cross reactivity remains low.

NS1 was selected for the anti-POWV IgG ELISA. This test is supposed to be highly specific.

(mature sequence of POWV Glycoprotein E)
SEQ ID NO: 1
ASMRCTHLENRDFVTGTQGTTRVSLVLELGGCVTITAEGKPSIDVWLEDI

FQESPAETREYCLHAKLTNTKVEARCPTTGPATLPEEHQANMVCKRDQSD

RGWGNHCGFFGKGSIVACAKFECEEAKKAVGHVYDSTKITYVVKVEPHTG

DYLAANETNSNRKSAQFTVASEKVILRLGDYGDVSLTCKVASGIDVAQTV

```
VMSLDSSKDHLPSAWQVHRDWFEDLALPWKHKDNQDWNSVEKLVEFGPPH
AVKMDVFNLGDQTAVLLKSLAGVPLASVEGQKYHLKSGHVTCDVGLEKLK
LKGTTYSMCDKAKFKWKRVPVDSGHDTVVMEVSYTGSDKPCRIPVRAVAH
GVPAVNVAMLITPNPTIETNGGGFIEMQLPPGDNIIYVGDLSQQWFQKG
```

(mature sequence of POWV NS1)
SEQ ID NO: 2
```
GHMDYGCAIDPERMEIRCGEGLVVWKEVSEWYDGYAYHPESPDTLAQALR
EAFERGVCGVVPQNRLEMAMWRSTAPELNLVLSEGEANLTIVVDKTDPAD
YRGGTPMVLKKTGKESKVSWKSWGKSILWSVPDSPRRMMMGVDGVGECPL
YRRATGVFTVAEFGVGLRTKVFLDLRGEASKECDTGVMGAAVKNGKAIHT
DQSMWMSSFRNDTGTYIHELILTDLRNCTWPASHTIDNDGVLDSHLFLPV
TLAGPRSKYNRIPGYSEQVRGPWDQTPLRVVRDHCPGTSVRIDSHCDKRG
ASVRSTTESGKIIPEWCCRACELPPVTFRSGTDCWYAMEIRPVHSQGGLV
RSMVVALEVTWGNNEPYKYWPQLSTNGTAHGHPHEIILYYYELYPTMTVV
VVSVATFILLSMVGMAAGMCMCARRRCITPYELTPGATVPFLLSLICCIR
TAKA
```

(His-tagged POWV Glycoprotein E as used in examples)
SEQ ID NO: 3
```
ASMRCTHLENRDFVTGTQGTTRVSLVLELGGCVTITAEGKPSIDVWLEDI
FQESPAETREYCLHAKLTNTKVEARCPTTGPATLPEEHQANMVCKRDQSD
RGWGNHCGFFGKGSIVACAKFECEEAKKAVGHVYDSTKITYVVKVEPHTG
DYLAANETNSNRKSAQFTVASEKVILRLGDYGDVSLTCKVASGIDVAQTV
VMSLDSSKDHLPSAWQVHRDWFEDLALPWKHKDNQDWNSVEKLVEFGPPH
AVKMDVFNLGDQTAVLLKSLAGVPLASVEGQKYHLKSGHVTCDVGLEKLK
LKGTTYSMCDKAKFKWKRVPVDSGHDTVVMEVSYTGSDKPCRIPVRAVAH
GVPAVNVAMLITPNPTIETNGGGFIEMQLPPGDNIIYVGDLSQQWFQKGL
EHHHHHHHH
```

(His-tagged POWV NS1 as used in examples)
SEQ ID NO: 4
```
GHMDYGCAIDPERMEIRCGEGLVVWKEVSEWYDGYAYHPESPDTLAQALR
EAFERGVCGVVPQNRLEMAMWRSTAPELNLVLSEGEANLTIVVDKTDPA
DYRGGTPMVLKKTGKESKVSWKSWGKSILWSVPDSPRRMMMGVDGVGECP
LYRRATGVFTVAEFGVGLRTKVFLDLRGEASKECDTGVMGAAVKNGKAIH
TDQSMWMSSFRNDTGTYIHELILTDLRNCTWPASHTIDNDGVLDSHLFLP
VTLAGPRSKYNRIPGYSEQVRGPWDQTPLRVVRDHCPGTSVRIDSHCDKR
GASVRSTTESGKIIPEWCCRACELPPVTFRSGTDCWYAMEIRPVHSQGGL
VRSMVVALEVTWGNNEPYKYWPQLSTNGTAHGHPHEIILYYYELYPTMTV
VVVSVATFILLSMVGMAAGMCMCARRRCITPYELTPGATVPFLLSLICCI
RTAKALEHHHHHHHH
```

(Variant of SEQ ID NO: 1)
SEQ ID NO: 5
EDLALPWKHKDNQD (Variant of SEQ ID NO: 1)
SEQ ID NO: 6
DLALPWKHKDNQ (Variant of SEQ ID NO: 1)
SEQ ID NO: 7
LALPWKHKDNQD (Variant of SEQ ID NO: 1)
SEQ ID NO: 8
ALPWKHKDNQDW (Variant of SEQ ID NO: 1)
SEQ ID NO: 9
LPWKHKDNQDWN (Variant of SEQ ID NO: 1)
SEQ ID NO: 10
PWKHKDNQDWNS (Zika virus NS1 antigen; SEQ ID NO: 1 from WO 2017/144174)
SEQ ID NO: 11
```
DVGCSVDFSKKETRCGTGVFVYNDVEAWRDRYKYHPDSPRRLAAAVKQAW
EEGICGISSVSRMENIMWKSVEGELNAILEENGVQLTVVVGSVKNPMWRG
PQRLPVPVNELPHGWKAWGKSYFVRAAKTNNSFVVDGDTLKECPLKHRAW
NSFLVEDHGFGVFHTSVWLKVREDYSLECDPAVIGTAVKGKEAAHSDLGY
WIESEKNDTWRLKRAHLIEMKTCEWPKSHTLWTDGVEESDLIIPKSLAGP
LSHHNTREGYRTQVKGPWHSEELEIRFEECPGTKVHVEETCGTRGPSLRS
TTASGRVIEEWCCRECTMPPLSFRAKDGCWYGMEIRPRKEPESNLVRSMV
TA
```

(Dengue virus 1 NS1 antigen; SEQ ID NO: 2 from WO 2017/144174)
SEQ ID NO: 12
```
DSGCVINWKGRELKCGSGIFVTNEVHTWTEQYKFQADSPKRLSAAIGKAW
EEGVCGIRSATRLENIMWKQISNELNHILLENDMKFTVVVGDASGILAQG
KKMIRPQPMEHKYSWKSWGKAKIIGADIQNTTFIIDGPDTPECSDDQRAW
NIWEVEDYGFGIFTTNIWLKLRDSYTQMCDHRLMSAAIKDSKAVHADMGY
WIESEKNETWKLARASFIEVKTCIWPKSHTLWSNGVLESEMIIPKIYGGP
ISQHNYRPGYFTQTAGPWHLGKLELDFDLCEGTTVIVDEHCGNRGPSLRT
TTVTGKIIHEWCCRSCTLPPLRFRGEDGCWYGMEIRPVKEKEENLVKSMV
SA
```

(Dengue virus 2 NS1 antigen; SEQ ID NO: 3 from WO 2017/144174)
SEQ ID NO: 13
```
DSGCVVSWKNKELKCGSGIFITDNVHTWTEQYKFQPESPSKLASAIQKAQ
EEGICGIRSVTRLENLMWKQITPELNHILAENEVKLTIMTGDIKGIMQAG
KRSLRPQPTELKYSWKTWGKAKMLSTESHNQTFLIDGPETAECPNTNRAW
NSLEVEDYGFGVFTTNIWLKLKEKQDAFCDSKLMSAAIKDNRAVHADMGY
WIESALNDTWKIEKASFIEVKNCHWPKSHTLWSNGVLESEMIIPKNLAGP
VSQHNYRPGYHTQIAGPWHLGKLEMDFDFCDGTTVVVTEDCGNRGPSLRT
TTASGKLITEWCCRSCTLPPLRYRGEDGCWYGMEIRPLKEKEENLVNSLV
TA
```

(Dengue virus 3 NS1 antigen; SEQ ID NO: 4 from WO 2017/144174)

SEQ ID NO: 14

DMGCVINWKGKELKCGSGIFVTNEVHTWTEQYKFQADSPKRLATAIAGAW
ENGVCGIRSTTRMENLLWKQIANELNHILWENNIKLTVVVGDIIGVLEQG
KRTLTPQPMELKYSWKIWGKAKIVTAETQNSSFIIDGPNTPECPSASRAW
NVWEVEDYGFGVFTTNIWLKLREVYTQSCDHRLMSAAIKDERAVHADMGY
WIESQKNGSWKLEKASLIEVKTCTWPKSHTLWSNGVLESDMIIPKSLAGP
ISQHNHRPGYHTQTAGPWHLGKLELDFNYCEGTTVVITENCGTRGPSLRT
TTVSGKLIHEWCCRSCTLPPLRYMGEDGCWYGMEIRPINEKEENMVKSLA
SA (Dengue virus 4 NS1 antigen; SEQ ID NO: 5 from WO 2017/144174)

SEQ ID NO: 15

DTGCAVSWSGKELKCGSGIFVVDNVHTWTEQYKFQPESPARLASAILNAH
KDGVCGIRSTTRLENVMWKQITNELNYVLWEGGHDLTVVAGDVKGVLTKG
KRALTPPVNDLKYSWKTWGKAKIFTPEARNSTFLIDGPDTSECPNERRAW
NSLEVEDYGFGMFTTNIWMKFREGSSEVCDHRLMSAAIKDQKAVHADMGY
WIESSKNQTWQIEKASLIEVKTCLWPKTHTLWSNGVLESQMLIPKSYAGP
FSQHNYRQGYATQTVGPWHLGKLEIDFGECPGTTVTIQEDCDHRGPSLRT
TTASGKLVTQWCCRSCTMPPLRFLGEDGCWYGMEIRPLSEKEENMVKSQV
SA (West Nile virus NS1 antigen; SEQ ID NO: 6 from WO 2017/144174)

SEQ ID NO: 16

DTGCAIDIGRQELRCGSGVFIHNDVEAWMDRYKFYPETPQGLAKIIQKAH
AEGVCGLRSVSRLEHQMWEAIKDELNTLLKENGVDLSVVVEKQNGMYKAA
PKRLAATTEKLEMGWKAWGKSIIFAPELANNTFVIDGPETEECPTANRAW
NSMEVEDFGFGLTSTRMFLRIRETNTTECDSKIIGTAVKNNMAVHSDLSY
WIESGLNDTWKLERAVLGEVKSCTWPETHTLWGDGVLESDLIIPITLAGP
RSNHNRRPGYKTQNQGPWDEGRVEIDFDYCPGTTVTISDSCEHRGPAART
TTESGKLITDWCCRSCTLPPLRFQTENGCWYGMEIRPTRHDEKTLVQSRV
NA (Tick-borne encephalitis virus NS1 antigen; SEQ ID NO: 7 from WO 2017/144174)

SEQ ID NO: 17

DVGCAVDTERMELRCGEGLVVWREVSEWYDNYAYYPETPGALASAIKETF
EEGTCGIVPQNRLEMAMWRSSATELNLALAEGDANLTVVVDKLDPTDYRG
GIPGLLKKGKDIKVSWKSWGHSMIWSIPEAPRRFMVGTEGSSECPLERRK
TGVFTVAEFGVGLRTKVFLDFRQESTHECDTGVMGAAVKNGMAVHTDQSL
WMKSVRNDTGTYIVELLVTDLRNCSWPASHTIDNAEVVDSELFLPASLAG
PRSWYNRIPGYSEQVKGPWKYSPIRVTREECPGTRVTINADCDKRGASVR
STTESGKVIPEWCCRTCTLPPVTFRTGTDCWYAMEIRPVHDQGGLVRSMV
VA (Japanese encephalitis virus NS1 antigen; SEQ ID NO: 8 from WO 2017/144174)

SEQ ID NO: 18

DTGCAIDITRKEMRCGSGIFVHNDVEAWVDRYKYLPETPRSLAKIVHKAH
QEGVCGVRSVTRLEHQMWESVRDELNVLLKENAVDLSVVVNKPVGRYRSA
PKRLSMTQEKFEMGWKAWGKSILFAPELANSTFVVDGPETKECPDERRAW
NSMQIEDFGFGITSTRVWLKIREENTDECDGAIIGTAVKGHVAVHSDLSY
WIESRLNDTWKLERAVFGEVKSCTWPETHTLWGDGVEESELIIPHTIAGP
RSKHNRREGYKTQNQGPWDENGIVLDFDYCPGTKVTITEDCGKRGPSIRT
TTDSGKLITDWCCRSCSLPPLRFRTENGCWYGMEIRPVRHDETTLVRSQV
DA (Yellow fever virus NS1 antigen; SEQ ID NO: 9 from WO 2017/144174)

SEQ ID NO: 19

DQGCAINFGKRELKCGDGIFIFRDSDDWLNKYSYYPEDPVKLASIVKASF
EEGKCGLNSVDSLEHEMWRSRADEINAILEENEVDISVVVQDPKNVYQRG
THPFSRIRDGLQYGWKTWGKNLVFSPGRKNGSFIIDGKSREKECPFSNRVW
NSFQIEEFGTGVFTTRVYMDAVFEYTIDCDGSILGAAVNGKKSAHGSPTF
WMGSHEVNGTWMIHTLEALDYKECEWPPTHTIGTSVEESEMFMPRSIGGP
VSSHNHIPGYKVQTNGPWMQVPLEVKREACPGTSVIIDGNCDGRGKSTRS
TTDSGKIIPEWCCRSCTMPPVSFHGSDGCWYPMEIRPRKTHESHLVRSWV
TA (Zika virus envelope glycoprotein; SEQ ID NO: 11 from WO 2017/144174)

SEQ ID NO: 20

IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFTCSKKMTGKSIQPENLEYRIMLSVHGSQHSG
MIGYETDEDRAKVEVTPNSPRAEATLGGFGSLGLDCEPRTGLDFSDLYYL
TMNNKHWLVHKEWFHDIPLPWHAGADTGTPHWNNKEALVEFKDAHAKRQT
VVVLGSQEGAVHTALAGALEAEMDGAKGRLFSGHLKCRLKMDKLRLKGVS
YSLCTAAFTFTKVPAETLHGTVTVEVQYAGTDGPCKIPVQMAVDMQTLTP
VGRLITANPVITESTENSKMMLELDPPFGDSYIVIGVGDKKITHHWHRSG
STIGKAFEATVRGAKRMAVLGDTAWDFGSVGGVFNSLGKGIHQIFGAAFK
SLFGGMSWFSQILIGTLLVWLGLNTKNGSISLTCLALGGVMIFLSTAVSA (Dengue virus 1 envelope glycoprotein; SEQ ID NO: 12 from WO 2017/144174)

SEQ ID NO: 21

MRCVGIGSRDFVEGLSGATWVDVVLEHGSCVTTMAKDKPTLDIELLKTEV
TNPAVLRKLCIEAKISNTTTDSRCPTQGEATLVEEQDANFVCRRTFVDRG
WGNGCGLFGKGSLLTCAKFKCVTKLEGKIVQYENLKYSVIVTVHTGDQHQ
VGNETTEHGTIATITPQAPTSEIQLTDYGALTLDCSPRTGLDFNEMVLLT
MKEKSWLVHKQWFLDLPLPWTSGASTSQETWNRQDLLVTFKTAHAKKQEV
VVLGSQEGAMHTALTGATEIQTSGTTTIFAGHLKCRLKMDKLTLKGMSYV
MCTGSFKLEKEVAETQHGTVLVQVKYEGTDAPCKIPFSTQDEKGVTQNRL
ITANPIVTDKEKPVNIETEPPFGESYIVVGAGEKALKQCWFKKGSSIGKM

-continued

FEATARGARRMAILGDTAWDFGSIGGVFTSVGKLVHQVFGTAYGVLFSGV

SWTMKIGIGILLTWLGLNSRSTSLSMTCIAVGMVTLYLGVMVQA (Dengue virus 2 envelope glycoprotein; SEQ ID NO: 13 from WO 2017/144174)

SEQ ID NO: 22
MRCIGISNRDFVEGVSGGSWVDIVLEHGSCVTTMAKNKPTLDFELIETEA

KQPATLRKYCIEAKLTNTTTDSRCPTQGEPSLNEEQDKRFVCKHSMVDRG

WGNGCGLFGKGGIVTCAMFTCKKNMKGKVVQPENLEYTIVITPHSGEEHA

VGNDTGKHGKEIKITPQSSITEAELTGYGTVTMECSPRTGLDFNEMVLLQ

MENKAWLVHRQWFLDLPLPWLPGADTQGSNWIQKETLVTFKNPHAKKQDV

VVLGSQEGAMHTALTGATEIQMSSGNLLFTGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVEPGQLKLNWFKKGSSIGQ

MIETTMRGAKRMAILGDTAWDFGSLGGVFTSIGKALHQVFGAIYGAAFSG

VSWIMKILIGVIITWIGMNSRSTSLSVSLVLVGVVTLYLGVMVQA (Dengue virus 3 envelope glycoprotein; SEQ ID NO: 14 from WO 2017/144174)

SEQ ID NO: 23
MRCVGVGNRDFVEGLSGATWVDVVLEHGGCVTTMAKNKPTLDIELQKTEA

TQLATLRKLCIEGKITNITTDSRCPTQGEAILPEEQDQNYVCKHTYVDRG

WGNGCGLFGKGSLVTCAKFQCLESIEGKVVQHENLKYTVIITVHTGDQHQ

VGNETQGVTAEITSQASTAEAILPEYGTLGLECSPRTGLDFNEMILLTMK

NKAWMVHRQWFFDLPLPWTSGATTKTPTWNRKELLVTFKNAHAKKQEVVV

LGSQEGAMHTALTGATEIQTSGGTSIFAGHLKCRLKMDKLKLKGMSYAMC

LNTFVLKKEVSETQHGTILIKVEYKGEDAPCKIPFSTEDGQGKAHNGRLI

TANPVVTKKEEPVNIEAEPPFGESNIVIGIGDKALKINWYRKGSSIGKMF

EATARGARRMAILGDTAWDFGSVGGVLNSLGKMVHQIFGSAYTALFSGVS

WIMKIGIGVLLTWIGLNSKNTSMSFSCIAIGIITLYLGVVVQA (Dengue virus 4 envelope glycoprotein; SEQ ID NO: 15 from WO 2017/144174)

SEQ ID NO: 24
MRCVGVGNRDFVEGVSGGAWVDLVLEHGGCVTTMAQGKPTLDFELTKTTA

KEVALLRTYCIEASISNITTATRCPTQGEPYLKEEQDQQYICRRDVVDRG

WGNGCGLFGKGGVVTCAKFSCSGKITGNLVQIENLEYTVVVTVHNGDTHA

VGNDTSNHGVTAMITPRSPSVEVKLPDYGELTLDCEPRSGIDFNEMILMK

MKKKTWLVHKQWFLDLPLPWTAGADTSEVHWNYKERMVTFKVPHAKRQDV

TVLGSQEGAMHSALAGATEVDSGDGNHMFAGHLKCKVRMEKLRIKGMSYT

MCSGKFSIDKEMAETQHGTTVVKVKYEGAGAPCKVPIEIRDVNKEKVVGR

IISSTPLAENTNSVTNIELEPPFGDSYIVIGVGNSALTLHWFRKGSSIGK

MFESTYRGAKRMAILGETAWDFGSVGGLFTSLGKAVHQVFGSVYTTMFGG

VSWMIRILIGFLVLWIGTNSRNTSMAMTCIAVGGITLFLGFTVQA (West Nile virus envelope glycoprotein; SEQ ID NO: 16 from WO 2017/144174)

SEQ ID NO: 25
FNCLGMSNRDFLEGVSGATWVDLVLEGDSCVTIMSKDKPTIDVKMMNMEA

ANLADVRSYCYLASVSDLSTRAACPTMGEAHNEKRADPAFVCKQGVVDRG

WGNGCGLFGKGSIDTCAKFACTTKATGWIIQKENIKYEVAIFVHGPTTVE

SHGKIGATQAGRFSITPSAPSYTLKLGEYGEVTVDCEPRSGIDTSAYYVM

SVGEKSFLVHREWFMDLNLPWSSAGSTTWRNRETLMEFEEPHATKQSVVA

LGSQEGALHQALAGAIPVEFSSNTVKLTSGHLKCRVKMEKLQLKGTTYGV

CSKAFKFARTPADTGHGTVVLELQYTGTDGPCKVPISSVASLNDLTPVGR

LVTVNPFVSVATANSKVLIELEPPFGDSYIVVGRGEQQINHHWHKSGSSI

GKAFTTTLRGAQRLAALGDTAWDFGSVGGVFTSVGKAIHQVFGGAFRSLF

GGMSWITQGLLGALLLWMGINARDRSIAMTFLAVGGVLLFLSVNVHA (Tick-borne encephalitis virus envelope glycoprotein; SEQ ID NO: 17 from WO 2017/144174)

SEQ ID NO: 26
SRCTHLENRDFVTGTQGTTRVTLVLELGGCVTITAEGKPSMDVWLDAIYQ

EKPAKTREYCLHAKLSDTKVAARCPTMGPATLTEEHQGGTVCKRDQSDRG

WGNHCGLFGKGSIVACVKAACEAKKKATGHVYDANRIVYTVKVEPHTGDY

VAANETHSGRKTASFTVSSEKTILTMGEYGDVSLLCRVASGVDLAQTVIL

ELDKTVEHLPTAWQVHRDWFNDLALPWKHEGAQNWNNAERLVEFGAPHAV

KMDVYNLGDQTGVLLKALAGVPVAHIEGTKYHLKSGHVTCEVGLEKLKMK

GLTYTMCDKTKFTWKRAPTDSGHDTVVMEVTFSGTKPCRIPVRAVAHGSP

DVNVAMLITPNPTIENNGGGFIEMQLPPGDNIIYVGELSHQWFQKGSSIG

RVFQKTKKGIERLTVIGEHAWDFGSAGGFLSSIGKAVHTVLGGAFNSIFG

GVGFLPKLLLGVALAWLGLNMRNPTMSMSFLLAGGLVLAMTLGVGA (Japanese encephalitis virus envelope glycoprotein; SEQ ID NO: 18 from WO 2017/144174)

SEQ ID NO: 27
FNCLGMGNRDFIEGASGATWVDLVLEGDSCLTIMANDKPTLDVRMINIEA

SQLAEVRSYCYHASVTDISTVARCPTTGEAHNEKRADSSYVCKQGFTDRG

WGNGCGLFGKGSIDTCAKFSCTSKAIGRTIQPENIKYEVGIFVHGTTTSE

NHGNYSAQVGASQAAKFTVTPNAPSITLKLGDYGEVTLDCEPRSGLNTEA

FYVMTVGSKSFLVHREWFHDLALPWTSPSSTAWRNRELLMEFEEAHATKQ

SVVALGSQEGGLHQALAGAIVVEYSSSVKLTSGHLKCRLKMDKLALKGTT

YGMCTEKFSFAKNPADTGHGTVVIELSYSGSDGPCKIPIVSVASLNDMTP

VGRLVTVNPFVATSSANSKVLVEMEPPFGDSYIVVGRGDKQINHHWHKAG

STLGKAFSTTLKGAQRLAALGDTAWDFGSIGGVFNSIGKAVHQVFGGAFR

TLFGGMSWITQGLMGALLLWMGVNARDRSIALAFLATGGVLVFLATNVHA (Yellow fever virus envelope glycoprotein; SEQ ID NO: 27 from WO 2017/144174)

SEQ ID NO: 28
AHCIGITDRDFIEGVHGGTWVSATLEQDKCVTVMAPDKPSLDISLETVAI

DGPAEARKVCYNAVLTHVKINDKCPSTGEAHLAEENEGDNACKRTYSDRG

WGNGCGLFGKGSIVACAKFTCAKSMSLFEVDQTKIQYVIRAQLHVGAKQE

NWNTDIKTLKFDALSGSQEAEFTGYGKATLECQVQTAVDFGNSYIAEMEK

ESWIVDRQWAQDLTLPWQSGSGGVWREMHHLVEFEPPHAATIRVLALGNQ

EGSLKTALTGAMRVTKDTNDNNLYKLHGGHVSCRVKLSALTLKGTSYKMC

TDKMSFVKNPTDTGHGTVVMQVKVPKGAPCKIPVIVADDLTAAINKGILV

-continued

TVNPIASTNDDEVLIEVNPPFGDSYIIVGTGDSRLTYQWHKEGSSIGKLF

TQTMKGAERLAVMGDAAWDFSSAGGFFTSVGKGIHTVFGSAFQGLFGGLN

WITKVIMGAVLIWVGINTRNMTMSMSMILVGVIMMFLSLGVGA (Powassan virus NS1 antigen; SEQ ID NO: 19 from WO 2017/144174)

SEQ ID NO: 29
DYGCAIDPERMEIRCGEGLVVWKEVSEWYDGYAYHPESPDTLAQALREAF

ERGVCGVVPQNRLEMAMWRSTAPELNLVLSEGEANLTIVVDKTDPADYRG

GTPMVLKKTGKESKVSWKSWGKSILWSVPDSPRRMMMGVDGVGECPLYRR

ATGVFTVAEFGVGLRTKVFLDLRGEASKECDTGVMGAAVKNGKAIHTDQS

MWMSSFRNDTGTYIHELILTDLRNCTWPASHTIDNDGVLDSHLFLPVTLA

GPRSKYNRIPGYSEQVRGPWDQTPLRVVRDHCPGTSVRIDSHCDKRGASV

RSTTESGKIIPEWCCRACELPPVTFRSGTDCWYAMEIRPVHSQGGLVRSM

VVA

The invention claimed is:

1. A recombinant or chemically-synthesized polypeptide, comprising:
   SEQ ID NO: 1 or a variant thereof.

2. A diagnostically useful carrier, comprising:
   a polypeptide capable of specifically capturing an antibody to SEQ ID NO: 1 in a sample from a subject.

3. The diagnostically useful carrier according to claim 2, wherein the diagnostically useful carrier is selected from the group consisting of a bead, a test strip, a microtiter plate, a membrane, a lateral flow device, a glass surface, a slide, a microarray, and a biochip.

4. A kit, comprising:
   the recombinant or chemically-synthesized polypeptide according to claim 1, or
   a diagnostically useful carrier optionally further comprising
     a polypeptide capable of specifically detecting a captured antibody to SEQ ID NO: 1, and/or
     a polypeptide capable of specifically detecting a captured antibody to SEQ ID NO: 2.

5. The kit according to claim 4, comprising the polypeptide capable of specifically detecting a captured antibody to SEQ ID NO: 1, and wherein the polypeptide capable of specifically detecting a captured antibody to SEQ ID NO: 1 is a secondary antibody recognizing IgM class antibodies.

6. The kit according to claim 4, comprising the polypeptide capable of specifically detecting a captured antibody to SEQ ID NO: 2, and wherein the polypeptide capable of specifically detecting a captured antibody to SEQ ID NO: 2 is a secondary antibody recognizing IgG or IgM class antibodies.

7. The kit according to claim 4, wherein the kit further comprises:
   a recombinant or monoclonal antibody to SEQ ID NO: 2, and/or
   a recombinant or monoclonal antibody to SEQ ID NO: 1.

8. A method for diagnosing, prognosing, or monitoring the treatment of a virus, the method comprising:
   detecting, in a sample from a subject having or suspected of having Flavivirus, the presence or absence of an antibody to SEQ ID NO: 1 and/or an antibody to SEQ ID NO: 2.

9. A method for distinguishing a Powassan virus infection from another viral infection, the method comprising:
   detecting, in a sample from a subject, the presence or absence of an antibody to SEQ ID NO: 1 and/or an antibody to SEQ ID NO: 2.

10. A method, comprising:
    immobilizing on a diagnostically useful carrier a polypeptide capable of specifically capturing an antibody to SEQ ID NO: 1 and/or a polypeptide capable of specifically capturing an antibody to SEQ ID NO: 2.

11. A method, comprising:
    manufacturing a kit for the diagnosis of a Flavivirus with a polypeptide comprising SEQ ID NO: 1 and/or SEQ ID NO: 2 or a variant thereof for the diagnosis of a Flavivirus.

12. The method according to claim 8, wherein the antibody to SEQ ID NO: 2 is an IgG or IgM class antibody.

13. The method according to claim 8, wherein the antibody to SEQ ID NO: 1 is an IgM class antibody.

14. A method, comprising:
   capturing an antibody to SEQ ID NO: 1 with an IgM antibody or a polypeptide capable of specifically capturing an IgM class antibody to SEQ ID NO: 1 for increasing the diagnostic reliability.

15. The method according to claim 8, wherein the sample is a blood or cerebrospinal fluid sample.

16. The diagnostically useful carrier according to claim 2, further comprising:
   a polypeptide capable of capturing an antibody to SEQ ID NO: 2.

17. The diagnostically useful carrier according to claim 3, wherein the bead is a paramagnetic bead, and wherein the membrane is selected from the group consisting of western blot, line blot, and dot blot.

18. The kit according to claim 6, wherein the polypeptide capable of detecting a captured antibody to SEQ ID NO: 2 is a secondary antibody recognizing IgG class antibodies.

19. The method according to claim 8, wherein the treatment is for Powassan virus infection, and wherein the method further comprises
   detecting in the sample from a subject the presence or absence of an antibody to SEQ ID NO: 1.

20. The method according to claim 9, wherein Powassan virus infection is distinguished from a Flavivirus infection other than Powassan virus, and wherein the antibody is to SEQ ID NO: 1 only.

* * * * *

SEQUENCE LISTING

<160> NUMBER OF SEQ ID NOS: 29

<210> SEQ ID NO 1
<211> LENGTH: 399
<212> TYPE: PRT
<213> ORGANISM: Powassan virus

<400> SEQUENCE: 1

Ala Ser Met Arg Cys Thr His Leu Glu Asn Arg Asp Phe Val Thr Gly
1               5                   10                  15

Thr Gln Gly Thr Thr Arg Val Ser Leu Val Leu Glu Leu Gly Gly Cys
            20                  25                  30

Val Thr Ile Thr Ala Glu Gly Lys Pro Ser Ile Asp Val Trp Leu Glu
        35                  40                  45

Asp Ile Phe Gln Glu Ser Pro Ala Glu Thr Arg Glu Tyr Cys Leu His
    50                  55                  60

Ala Lys Leu Thr Asn Thr Lys Val Glu Ala Arg Cys Pro Thr Thr Gly
65                  70                  75                  80

Pro Ala Thr Leu Pro Glu Glu His Gln Ala Asn Met Val Cys Lys Arg
                85                  90                  95

Asp Gln Ser Asp Arg Gly Trp Gly Asn His Cys Gly Phe Phe Gly Lys
            100                 105                 110

Gly Ser Ile Val Ala Cys Ala Lys Phe Glu Cys Glu Glu Ala Lys Lys
        115                 120                 125

Ala Val Gly His Val Tyr Asp Ser Thr Lys Ile Thr Tyr Val Val Lys
    130                 135                 140

Val Glu Pro His Thr Gly Asp Tyr Leu Ala Ala Asn Glu Thr Asn Ser
145                 150                 155                 160

Asn Arg Lys Ser Ala Gln Phe Thr Val Ala Ser Glu Lys Val Ile Leu
                165                 170                 175

Arg Leu Gly Asp Tyr Gly Asp Val Ser Leu Thr Cys Lys Val Ala Ser
            180                 185                 190

Gly Ile Asp Val Ala Gln Thr Val Val Met Ser Leu Asp Ser Ser Lys
        195                 200                 205

Asp His Leu Pro Ser Ala Trp Gln Val His Arg Asp Trp Phe Glu Asp
    210                 215                 220

Leu Ala Leu Pro Trp Lys His Lys Asp Asn Gln Asp Trp Asn Ser Val
225                 230                 235                 240

Glu Lys Leu Val Glu Phe Gly Pro Pro His Ala Val Lys Met Asp Val
                245                 250                 255

Phe Asn Leu Gly Asp Gln Thr Ala Val Leu Leu Lys Ser Leu Ala Gly
            260                 265                 270

Val Pro Leu Ala Ser Val Glu Gly Gln Lys Tyr His Leu Lys Ser Gly

```
            275                 280                 285
His Val Thr Cys Asp Val Gly Leu Glu Lys Leu Lys Leu Lys Gly Thr
    290                 295                 300

Thr Tyr Ser Met Cys Asp Lys Ala Lys Phe Lys Trp Lys Arg Val Pro
305                 310                 315                 320

Val Asp Ser Gly His Asp Thr Val Val Met Glu Val Ser Tyr Thr Gly
                325                 330                 335

Ser Asp Lys Pro Cys Arg Ile Pro Val Arg Ala Val Ala His Gly Val
                340                 345                 350

Pro Ala Val Asn Val Ala Met Leu Ile Thr Pro Asn Pro Thr Ile Glu
                355                 360                 365

Thr Asn Gly Gly Gly Phe Ile Glu Met Gln Leu Pro Pro Gly Asp Asn
            370                 375                 380

Ile Ile Tyr Val Gly Asp Leu Ser Gln Gln Trp Phe Gln Lys Gly
385                 390                 395

<210> SEQ ID NO 2
<211> LENGTH: 454
<212> TYPE: PRT
<213> ORGANISM: Powassan virus

<400> SEQUENCE: 2

Gly His Met Asp Tyr Gly Cys Ala Ile Asp Pro Glu Arg Met Glu Ile
1               5                   10                  15

Arg Cys Gly Glu Gly Leu Val Val Trp Lys Glu Val Ser Glu Trp Tyr
                20                  25                  30

Asp Gly Tyr Ala Tyr His Pro Glu Ser Pro Asp Thr Leu Ala Gln Ala
            35                  40                  45

Leu Arg Glu Ala Phe Glu Arg Gly Val Cys Gly Val Val Pro Gln Asn
        50                  55                  60

Arg Leu Glu Met Ala Met Trp Arg Ser Thr Ala Pro Glu Leu Asn Leu
65                  70                  75                  80

Val Leu Ser Glu Gly Glu Ala Asn Leu Thr Ile Val Val Asp Lys Thr
                85                  90                  95

Asp Pro Ala Asp Tyr Arg Gly Gly Thr Pro Met Val Leu Lys Lys Thr
            100                 105                 110

Gly Lys Glu Ser Lys Val Ser Trp Lys Ser Trp Gly Lys Ser Ile Leu
        115                 120                 125

Trp Ser Val Pro Asp Ser Pro Arg Arg Met Met Met Gly Val Asp Gly
130                 135                 140

Val Gly Glu Cys Pro Leu Tyr Arg Arg Ala Thr Gly Val Phe Thr Val
145                 150                 155                 160

Ala Glu Phe Gly Val Gly Leu Arg Thr Lys Val Phe Leu Asp Leu Arg
                165                 170                 175

Gly Glu Ala Ser Lys Glu Cys Asp Thr Gly Val Met Gly Ala Ala Val
            180                 185                 190

Lys Asn Gly Lys Ala Ile His Thr Asp Gln Ser Met Trp Met Ser Ser
        195                 200                 205

Phe Arg Asn Asp Thr Gly Thr Tyr Ile His Glu Leu Ile Leu Thr Asp
    210                 215                 220

Leu Arg Asn Cys Thr Trp Pro Ala Ser His Thr Ile Asp Asn Asp Gly
225                 230                 235                 240

Val Leu Asp Ser His Leu Phe Leu Pro Val Thr Leu Ala Gly Pro Arg
                245                 250                 255
```

```
Ser Lys Tyr Asn Arg Ile Pro Gly Tyr Ser Glu Gln Val Arg Gly Pro
        260                 265                 270

Trp Asp Gln Thr Pro Leu Arg Val Val Arg Asp His Cys Pro Gly Thr
        275                 280                 285

Ser Val Arg Ile Asp Ser His Cys Asp Lys Arg Gly Ala Ser Val Arg
    290                 295                 300

Ser Thr Thr Glu Ser Gly Lys Ile Ile Pro Glu Trp Cys Cys Arg Ala
305                 310                 315                 320

Cys Glu Leu Pro Pro Val Thr Phe Arg Ser Gly Thr Asp Cys Trp Tyr
                325                 330                 335

Ala Met Glu Ile Arg Pro Val His Ser Gln Gly Gly Leu Val Arg Ser
        340                 345                 350

Met Val Val Ala Leu Glu Val Thr Trp Gly Asn Asn Glu Pro Tyr Lys
        355                 360                 365

Tyr Trp Pro Gln Leu Ser Thr Asn Gly Thr Ala His Gly His Pro His
        370                 375                 380

Glu Ile Ile Leu Tyr Tyr Tyr Glu Leu Tyr Pro Thr Met Thr Val Val
385                 390                 395                 400

Val Val Ser Val Ala Thr Phe Ile Leu Leu Ser Met Val Gly Met Ala
                405                 410                 415

Ala Gly Met Cys Met Cys Ala Arg Arg Arg Cys Ile Thr Pro Tyr Glu
                420                 425                 430

Leu Thr Pro Gly Ala Thr Val Pro Phe Leu Leu Ser Leu Ile Cys Cys
                435                 440                 445

Ile Arg Thr Ala Lys Ala
        450

<210> SEQ ID NO 3
<211> LENGTH: 409
<212> TYPE: PRT
<213> ORGANISM: Artificial Sequence
<220> FEATURE:
<223> OTHER INFORMATION: His-tagged Glycoprotein E

<400> SEQUENCE: 3

Ala Ser Met Arg Cys Thr His Leu Glu Asn Arg Asp Phe Val Thr Gly
1               5                   10                  15

Thr Gln Gly Thr Thr Arg Val Ser Leu Val Leu Glu Leu Gly Gly Cys
            20                  25                  30

Asn Arg Lys Ser Ala Gln Phe Thr Val Ala Ser Glu Lys Val Ile Leu
            165                 170                 175

Arg Leu Gly Asp Tyr Gly Asp Val Ser Leu Thr Cys Lys Val Ala Ser
        180                 185                 190

Gly Ile Asp Val Ala Gln Thr Val Val Met Ser Leu Asp Ser Ser Lys
        195                 200                 205

Asp His Leu Pro Ser Ala Trp Gln Val His Arg Asp Trp Phe Glu Asp
        210                 215                 220

Leu Ala Leu Pro Trp Lys His Lys Asp Asn Gln Asp Trp Asn Ser Val
225                 230                 235                 240

Glu Lys Leu Val Glu Phe Gly Pro Pro His Ala Val Lys Met Asp Val
                245                 250                 255

Phe Asn Leu Gly Asp Gln Thr Ala Val Leu Leu Lys Ser Leu Ala Gly
                260                 265                 270

Val Pro Leu Ala Ser Val Glu Gly Gln Lys Tyr His Leu Lys Ser Gly
            275                 280                 285

His Val Thr Cys Asp Val Gly Leu Glu Lys Leu Lys Leu Lys Gly Thr
        290                 295                 300

Thr Tyr Ser Met Cys Asp Lys Ala Lys Phe Lys Trp Lys Arg Val Pro
305                 310                 315                 320

Val Asp Ser Gly His Asp Thr Val Val Met Glu Val Ser Tyr Thr Gly
                325                 330                 335

Ser Asp Lys Pro Cys Arg Ile Pro Val Arg Ala Val Ala His Gly Val
                340                 345                 350

Pro Ala Val Asn Val Ala Met Leu Ile Thr Pro Asn Pro Thr Ile Glu
            355                 360                 365

Thr Asn Gly Gly Gly Phe Ile Glu Met Gln Leu Pro Pro Gly Asp Asn
        370                 375                 380

Ile Ile Tyr Val Gly Asp Leu Ser Gln Gln Trp Phe Gln Lys Gly Leu
385                 390                 395                 400

Glu His His His His His His His
            405

<210> SEQ ID NO 4
<211> LENGTH: 464
<212> TYPE: PRT
<213> ORGANISM: Artificial Sequence
<220> FEATURE:
<223> OTHER INFORMATION: His-tagged NS1

<400> SEQUENCE: 4

Gly His Met Asp Tyr Gly Cys Ala Ile Asp Pro Glu Arg Met Glu Ile
1               5                   10                  15

Arg Cys Gly Glu Gly Leu Val Val Trp Lys Glu Val Ser Glu Trp Tyr
            20                  25                  30

Asp Gly Tyr Ala Tyr His Pro Glu Ser Pro Asp Thr Leu Ala Gln Ala
        35                  40                  45

Leu Arg Glu Ala Phe Glu Arg Gly Val Cys Gly Val Val Pro Gln Asn
    50                  55                  60

Arg Leu Glu Met Ala Met Trp Arg Ser Thr Ala Pro Glu Leu Asn Leu
65                  70                  75                  80

Val Leu Ser Glu Gly Glu Ala Asn Leu Thr Ile Val Val Asp Lys Thr
                85                  90                  95

Asp Pro Ala Asp Tyr Arg Gly Gly Thr Pro Met Val Leu Lys Lys Thr
            100                 105                 110

```
Gly Lys Glu Ser Lys Val Ser Trp Lys Ser Trp Lys Ser Ile Leu
            115                 120                 125
Trp Ser Val Pro Asp Ser Pro Arg Met Met Met Gly Val Asp Gly
130                 135                 140
Val Gly Glu Cys Pro Leu Tyr Arg Arg Ala Thr Gly Val Phe Thr Val
145                 150                 155                 160
Ala Glu Phe Gly Val Gly Leu Arg Thr Lys Val Phe Leu Asp Leu Arg
                    165                 170                 175
Gly Glu Ala Ser Lys Glu Cys Asp Thr Gly Val Met Gly Ala Ala Val
                180                 185                 190
Lys Asn Gly Lys Ala Ile His Thr Asp Gln Ser Met Trp Met Ser Ser
            195                 200                 205
Phe Arg Asn Asp Thr Gly Thr Tyr Ile His Glu Leu Ile Leu Thr Asp
210                 215                 220
Leu Arg Asn Cys Thr Trp Pro Ala Ser His Thr Ile Asp Asn Asp Gly
225                 230                 235                 240
Val Leu Asp Ser His Leu Phe Leu Pro Val Thr Leu Ala Gly Pro Arg
                245                 250                 255
Ser Lys Tyr Asn Arg Ile Pro Gly Tyr Ser Glu Gln Val Arg Gly Pro
                260                 265                 270
Trp Asp Gln Thr Pro Leu Arg Val Val Arg Asp His Cys Pro Gly Thr
            275                 280                 285
Ser Val Arg Ile Asp Ser His Cys Asp Lys Arg Gly Ala Ser Val Arg
            290                 295                 300
Ser Thr Thr Glu Ser Gly Lys Ile Ile Pro Glu Trp Cys Cys Arg Ala
305                 310                 315                 320
Cys Glu Leu Pro Pro Val Thr Phe Arg Ser Gly Thr Asp Cys Trp Tyr
                325                 330                 335
Ala Met Glu Ile Arg Pro Val His Ser Gln Gly Gly Leu Val Arg Ser
                340                 345                 350
Met Val Val Ala Leu Glu Val Thr Trp Gly Asn Asn Glu Pro Tyr Lys
            355                 360                 365
Tyr Trp Pro Gln Leu Ser Thr Asn Gly Thr Ala His Gly His Pro His
370                 375                 380
Glu Ile Ile Leu Tyr Tyr Tyr Glu Leu Tyr Pro Thr Met Thr Val Val
385                 390                 395                 400
Val Val Ser Val Ala Thr Phe Ile Leu Leu Ser Met Val Gly Met Ala
                405                 410                 415
Ala Gly Met Cys Met Cys Ala Arg Arg Arg Cys Ile Thr Pro Tyr Glu
                420                 425                 430
Leu Thr Pro Gly Ala Thr Val Pro Phe Leu Leu Ser Leu Ile Cys Cys
            435                 440                 445
Ile Arg Thr Ala Lys Ala Leu Glu His His His His His His
450                 455                 460
```

```
<210> SEQ ID NO 5
<211> LENGTH: 14
<212> TYPE: PRT
<213> ORGANISM: Artificial Sequence
<220> FEATURE:
<223> OTHER INFORMATION: Variant of SEQ ID NO: 1

<400> SEQUENCE: 5
```

```
Glu Asp Leu Ala Leu Pro Trp Lys His Lys Asp Asn Gln Asp
1               5                   10
```

-continued

<210> SEQ ID NO 6
<211> LENGTH: 12
<212> TYPE: PRT
<213> ORGANISM: Artificial Sequence
<220> FEATURE:
<223> OTHER INFORMATION: Variant of SEQ ID NO: 1

<400> SEQUENCE: 6

```
Asp Leu Ala Leu Pro Trp Lys His Lys Asp Asn Gln
1               5                   10
```

<210> SEQ ID NO 7
<211> LENGTH: 12
<212> TYPE: PRT
<213> ORGANISM: Artificial Sequence
<220> FEATURE:
<223> OTHER INFORMATION: Variant of SEQ ID NO: 1

<400> SEQUENCE: 7

```
Leu Ala Leu Pro Trp Lys His Lys Asp Asn Gln Asp
1               5                   10
```

<210> SEQ ID NO 8
<211> LENGTH: 12
<212> TYPE: PRT
<213> ORGANISM: Artificial Sequence
<220> FEATURE:
<223> OTHER INFORMATION: Variant of SEQ ID NO: 1

<400> SEQUENCE: 8

```
Ala Leu Pro Trp Lys His Lys Asp Asn Gln Asp Trp
1               5                   10
```

<210> SEQ ID NO 9
<211> LENGTH: 12
<212> TYPE: PRT
<213> ORGANISM: Artificial Sequence
<220> FEATURE:
<223> OTHER INFORMATION: Variant of SEQ ID NO: 1

<400> SEQUENCE: 9

```
Leu Pro Trp Lys His Lys Asp Asn Gln Asp Trp Asn
1               5                   10
```

<210> SEQ ID NO 10
<211> LENGTH: 12
<212> TYPE: PRT
<213> ORGANISM: Artificial Sequence
<220> FEATURE:
<223> OTHER INFORMATION: Variant of SEQ ID NO: 1

<400> SEQUENCE: 10

```
Pro Trp Lys His Lys Asp Asn Gln Asp Trp Asn Ser
1               5                   10
```

<210> SEQ ID NO 11
<211> LENGTH: 352
<212> TYPE: PRT
<213> ORGANISM: Artificial Sequence
<220> FEATURE:
<223> OTHER INFORMATION: Zika virus NS1 antigen; SEQ ID NO: 1 from WO 2017/144174

<400> SEQUENCE: 11

```
Asp Val Gly Cys Ser Val Asp Phe Ser Lys Lys Glu Thr Arg Cys Gly
1               5                   10                  15
```

```
Thr Gly Val Phe Val Tyr Asn Asp Val Glu Ala Trp Arg Asp Arg Tyr
             20                  25                  30

Lys Tyr His Pro Asp Ser Pro Arg Arg Leu Ala Ala Val Lys Gln
         35                  40                  45

Ala Trp Glu Glu Gly Ile Cys Gly Ile Ser Ser Val Ser Arg Met Glu
 50                  55                  60

Asn Ile Met Trp Lys Ser Val Glu Gly Glu Leu Asn Ala Ile Leu Glu
 65                  70                  75                  80

Glu Asn Gly Val Gln Leu Thr Val Val Gly Ser Val Lys Asn Pro
             85                  90                  95

Met Trp Arg Gly Pro Gln Arg Leu Pro Val Pro Val Asn Glu Leu Pro
            100                 105                 110

His Gly Trp Lys Ala Trp Gly Lys Ser Tyr Phe Val Arg Ala Ala Lys
            115                 120                 125

Thr Asn Asn Ser Phe Val Val Asp Gly Asp Thr Leu Lys Glu Cys Pro
        130                 135                 140

Leu Lys His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
                165                 170                 175

Leu Glu Cys Asp Pro Ala Val Ile Gly Thr Ala Val Lys Gly Lys Glu
            180                 185                 190

Ala Ala His Ser Asp Leu Gly Tyr Trp Ile Glu Ser Glu Lys Asn Asp
        195                 200                 205

Thr Trp Arg Leu Lys Arg Ala His Leu Ile Glu Met Lys Thr Cys Glu
210                 215                 220

Trp Pro Lys Ser His Thr Leu Trp Thr Asp Gly Val Glu Glu Ser Asp
225                 230                 235                 240

Leu Ile Ile Pro Lys Ser Leu Ala Gly Pro Leu Ser His His Asn Thr
                245                 250                 255

Arg Glu Gly Tyr Arg Thr Gln Val Lys Gly Pro Trp His Ser Glu Glu
            260                 265                 270

Leu Glu Ile Arg Phe Glu Glu Cys Pro Gly Thr Lys Val His Val Glu
        275                 280                 285

Glu Thr Cys Gly Thr Arg Gly Pro Ser Leu Arg Ser Thr Thr Ala Ser
290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr Ala
            340                 345                 350

<210> SEQ ID NO 12
<211> LENGTH: 352
<212> TYPE: PRT
<213> ORGANISM: Artificial Sequence
<220> FEATURE:
<223> OTHER INFORMATION: Dengue virus 1 NS1 antigen; SEQ ID NO: 2 from
      WO 2017/144174

<400> SEQUENCE: 12

Asp Ser Gly Cys Val Ile Asn Trp Lys Gly Arg Glu Leu Lys Cys Gly
1               5                   10                  15

Ser Gly Ile Phe Val Thr Asn Glu Val His Thr Trp Thr Glu Gln Tyr
            20                  25                  30
```

```
Lys Phe Gln Ala Asp Ser Pro Lys Arg Leu Ser Ala Ile Gly Lys
            35                  40                  45

Ala Trp Glu Glu Gly Val Cys Gly Ile Arg Ser Ala Thr Arg Leu Glu
 50                  55                  60

Asn Ile Met Trp Lys Gln Ile Ser Asn Glu Leu Asn His Ile Leu Leu
 65                  70                  75                  80

Glu Asn Asp Met Lys Phe Thr Val Val Gly Asp Ala Ser Gly Ile
                    85                  90                  95

Leu Ala Gln Gly Lys Lys Met Ile Arg Pro Gln Pro Met Glu His Lys
                100                 105                 110

Tyr Ser Trp Lys Ser Trp Gly Lys Ala Lys Ile Ile Gly Ala Asp Ile
            115                 120                 125

Gln Asn Thr Thr Phe Ile Ile Asp Gly Pro Asp Thr Pro Glu Cys Ser
        130                 135                 140

Asp Asp Gln Arg Ala Trp Asn Ile Trp Glu Val Glu Asp Tyr Gly Phe
145                 150                 155                 160

Gly Ile Phe Thr Thr Asn Ile Trp Leu Lys Leu Arg Asp Ser Tyr Thr
                165                 170                 175

Gln Met Cys Asp His Arg Leu Met Ser Ala Ala Ile Lys Asp Ser Lys
            180                 185                 190

Ala Val His Ala Asp Met Gly Tyr Trp Ile Glu Ser Glu Lys Asn Glu
        195                 200                 205

Thr Trp Lys Leu Ala Arg Ala Ser Phe Ile Glu Val Lys Thr Cys Ile
210                 215                 220

Trp Pro Lys Ser His Thr Leu Trp Ser Asn Gly Val Leu Glu Ser Glu
225                 230                 235                 240

Met Ile Ile Pro Lys Ile Tyr Gly Gly Pro Ile Ser Gln His Asn Tyr
                245                 250                 255

Arg Pro Gly Tyr Phe Thr Gln Thr Ala Gly Pro Trp His Leu Gly Lys
            260                 265                 270

Leu Glu Leu Asp Phe Asp Leu Cys Glu Gly Thr Thr Val Ile Val Asp
        275                 280                 285

Glu His Cys Gly Asn Arg Gly Pro Ser Leu Arg Thr Thr Thr Val Thr
290                 295                 300

Gly Lys Ile Ile His Glu Trp Cys Cys Arg Ser Cys Thr Leu Pro Pro
305                 310                 315                 320

Leu Arg Phe Arg Gly Glu Asp Gly Cys Trp Tyr Gly Met Glu Ile Arg
                325                 330                 335

Pro Val Lys Glu Lys Glu Glu Asn Leu Val Lys Ser Met Val Ser Ala
            340                 345                 350
```

<210> SEQ ID NO 13
<211> LENGTH: 352
<212> TYPE: PRT
<213> ORGANISM: Artificial Sequence
<220> FEATURE:
<223> OTHER INFORMATION: Dengue virus 2 NS1 antigen; SEQ ID NO: 3 from
      WO 2017/144174

<400> SEQUENCE: 13

```
Asp Ser Gly Cys Val Val Ser Trp Lys Asn Lys Glu Leu Lys Cys Gly
  1               5                  10                  15

Ser Gly Ile Phe Ile Thr Asp Asn Val His Thr Trp Thr Glu Gln Tyr
                 20                  25                  30

Lys Phe Gln Pro Glu Ser Pro Ser Lys Leu Ala Ser Ala Ile Gln Lys
```

```
            35                  40                  45
Ala Gln Glu Glu Gly Ile Cys Gly Ile Arg Ser Val Thr Arg Leu Glu
 50                  55                  60
Asn Leu Met Trp Lys Gln Ile Thr Pro Glu Leu Asn His Ile Leu Ala
 65                  70                  75                  80
Glu Asn Glu Val Lys Leu Thr Ile Met Thr Gly Asp Ile Lys Gly Ile
                     85                  90                  95
Met Gln Ala Gly Lys Arg Ser Leu Arg Pro Gln Pro Thr Glu Leu Lys
                100                 105                 110
Tyr Ser Trp Lys Thr Trp Gly Lys Ala Lys Met Leu Ser Thr Glu Ser
                115                 120                 125
His Asn Gln Thr Phe Leu Ile Asp Gly Pro Glu Thr Ala Glu Cys Pro
130                 135                 140
Asn Thr Asn Arg Ala Trp Asn Ser Leu Glu Val Glu Asp Tyr Gly Phe
145                 150                 155                 160
Gly Val Phe Thr Thr Asn Ile Trp Leu Lys Leu Lys Glu Lys Gln Asp
                165                 170                 175
Ala Phe Cys Asp Ser Lys Leu Met Ser Ala Ala Ile Lys Asp Asn Arg
                180                 185                 190
Ala Val His Ala Asp Met Gly Tyr Trp Ile Glu Ser Ala Leu Asn Asp
                195                 200                 205
Thr Trp Lys Ile Glu Lys Ala Ser Phe Ile Glu Val Lys Asn Cys His
                210                 215                 220
Trp Pro Lys Ser His Thr Leu Trp Ser Asn Gly Val Leu Glu Ser Glu
225                 230                 235                 240
Met Ile Ile Pro Lys Asn Leu Ala Gly Pro Val Ser Gln His Asn Tyr
                245                 250                 255
Arg Pro Gly Tyr His Thr Gln Ile Ala Gly Pro Trp His Leu Gly Lys
                260                 265                 270
Leu Glu Met Asp Phe Asp Phe Cys Asp Gly Thr Thr Val Val Val Thr
                275                 280                 285
Glu Asp Cys Gly Asn Arg Gly Pro Ser Leu Arg Thr Thr Thr Ala Ser
290                 295                 300
Gly Lys Leu Ile Thr Glu Trp Cys Cys Arg Ser Cys Thr Leu Pro Pro
305                 310                 315                 320
Leu Arg Tyr Arg Gly Asp Gly Cys Trp Tyr Gly Met Glu Ile Arg
                325                 330                 335
Pro Leu Lys Glu Lys Glu Glu Asn Leu Val Asn Ser Leu Val Thr Ala
                340                 345                 350

<210> SEQ ID NO 14
<211> LENGTH: 352
<212> TYPE: PRT
<213> ORGANISM: Artificial Sequence
<220> FEATURE:
<223> OTHER INFORMATION: Dengue virus 3 NS1 antigen; SEQ ID NO: 4 from
      WO 2017/144174

<400> SEQUENCE: 14

Asp Met Gly Cys Val Ile Asn Trp Lys Gly Lys Glu Leu Lys Cys Gly
 1               5                  10                  15
Ser Gly Ile Phe Val Thr Asn Glu Val His Thr Trp Thr Glu Gln Tyr
                20                  25                  30
Lys Phe Gln Ala Asp Ser Pro Lys Arg Leu Ala Thr Ala Ile Ala Gly
                35                  40                  45
```

```
Ala Trp Glu Asn Gly Val Cys Gly Ile Arg Ser Thr Thr Arg Met Glu
 50                  55                  60

Asn Leu Leu Trp Lys Gln Ile Ala Asn Glu Leu Asn His Ile Leu Trp
 65                  70                  75                  80

Glu Asn Asn Ile Lys Leu Thr Val Val Gly Asp Ile Ile Gly Val
                 85                  90                  95

Leu Glu Gln Gly Lys Arg Thr Leu Thr Pro Gln Pro Met Glu Leu Lys
                100                 105                 110

Tyr Ser Trp Lys Ile Trp Gly Lys Ala Lys Ile Val Thr Ala Glu Thr
                115                 120                 125

Gln Asn Ser Ser Phe Ile Ile Asp Gly Pro Asn Thr Pro Glu Cys Pro
    130                 135                 140

Ser Ala Ser Arg Ala Trp Asn Val Trp Glu Val Glu Asp Tyr Gly Phe
145                 150                 155                 160

Gly Val Phe Thr Thr Asn Ile Trp Leu Lys Leu Arg Glu Val Tyr Thr
                165                 170                 175

Gln Ser Cys Asp His Arg Leu Met Ser Ala Ala Ile Lys Asp Glu Arg
                180                 185                 190

Ala Val His Ala Asp Met Gly Tyr Trp Ile Glu Ser Gln Lys Asn Gly
                195                 200                 205

Ser Trp Lys Leu Glu Lys Ala Ser Leu Ile Glu Val Lys Thr Cys Thr
    210                 215                 220

Trp Pro Lys Ser His Thr Leu Trp Ser Asn Gly Val Leu Glu Ser Asp
225                 230                 235                 240

Met Ile Ile Pro Lys Ser Leu Ala Gly Pro Ile Ser Gln His Asn His
                245                 250                 255

Arg Pro Gly Tyr His Thr Gln Thr Ala Gly Pro Trp His Leu Gly Lys
                260                 265                 270

Leu Glu Leu Asp Phe Asn Tyr Cys Glu Gly Thr Thr Val Val Ile Thr
                275                 280                 285

Glu Asn Cys Gly Thr Arg Gly Pro Ser Leu Arg Thr Thr Thr Val Ser
    290                 295                 300

Gly Lys Leu Ile His Glu Trp Cys Cys Arg Ser Cys Thr Leu Pro Pro
305                 310                 315                 320

Leu Arg Tyr Met Gly Glu Asp Gly Cys Trp Tyr Gly Met Glu Ile Arg
                325                 330                 335

Pro Ile Asn Glu Lys Glu Glu Asn Met Val Lys Ser Leu Ala Ser Ala
                340                 345                 350

<210> SEQ ID NO 15
<211> LENGTH: 352
<212> TYPE: PRT
<213> ORGANISM: Artificial Sequence
<220> FEATURE:
<223> OTHER INFORMATION: Dengue virus 4 NS1 antigen; SEQ ID NO: 5 from
      WO 2017/144174

<400> SEQUENCE: 15

Asp Thr Gly Cys Ala Val Ser Trp Ser Gly Lys Glu Leu Lys Cys Gly
 1               5                  10                  15

Ser Gly Ile Phe Val Val Asp Asn Val His Thr Trp Thr Glu Gln Tyr
                20                  25                  30

Lys Phe Gln Pro Glu Ser Pro Ala Arg Leu Ala Ser Ala Ile Leu Asn
            35                  40                  45

Ala His Lys Asp Gly Val Cys Gly Ile Arg Ser Thr Thr Arg Leu Glu
 50                  55                  60
```

```
Asn Val Met Trp Lys Gln Ile Thr Asn Glu Leu Asn Tyr Val Leu Trp
 65                  70                  75                  80

Glu Gly Gly His Asp Leu Thr Val Val Ala Gly Asp Val Lys Gly Val
                 85                  90                  95

Leu Thr Lys Gly Lys Arg Ala Leu Thr Pro Pro Val Asn Asp Leu Lys
            100                 105                 110

Tyr Ser Trp Lys Thr Trp Gly Lys Ala Lys Ile Phe Thr Pro Glu Ala
        115                 120                 125

Arg Asn Ser Thr Phe Leu Ile Asp Gly Pro Asp Thr Ser Glu Cys Pro
    130                 135                 140

Asn Glu Arg Arg Ala Trp Asn Ser Leu Glu Val Glu Asp Tyr Gly Phe
145                 150                 155                 160

Gly Met Phe Thr Thr Asn Ile Trp Met Lys Phe Arg Glu Gly Ser Ser
                165                 170                 175

Glu Val Cys Asp His Arg Leu Met Ser Ala Ala Ile Lys Asp Gln Lys
            180                 185                 190

Ala Val His Ala Asp Met Gly Tyr Trp Ile Glu Ser Ser Lys Asn Gln
        195                 200                 205

Thr Trp Gln Ile Glu Lys Ala Ser Leu Ile Glu Val Lys Thr Cys Leu
    210                 215                 220

Trp Pro Lys Thr His Thr Leu Trp Ser Asn Gly Val Leu Glu Ser Gln
225                 230                 235                 240

Met Leu Ile Pro Lys Ser Tyr Ala Gly Pro Phe Ser Gln His Asn Tyr
                245                 250                 255

Arg Gln Gly Tyr Ala Thr Gln Thr Val Gly Pro Trp His Leu Gly Lys
            260                 265                 270

Leu Glu Ile Asp Phe Gly Glu Cys Pro Gly Thr Thr Val Thr Ile Gln
        275                 280                 285

Glu Asp Cys Asp His Arg Gly Pro Ser Leu Arg Thr Thr Thr Ala Ser
    290                 295                 300

Gly Lys Leu Val Thr Gln Trp Cys Cys Arg Ser Cys Thr Met Pro Pro
305                 310                 315                 320

Leu Arg Phe Leu Gly Glu Asp Gly Cys Trp Tyr Gly Met Glu Ile Arg
                325                 330                 335

Pro Leu Ser Glu Lys Glu Glu Asn Met Val Lys Ser Gln Val Ser Ala
            340                 345                 350

<210> SEQ ID NO 16
<211> LENGTH: 352
<212> TYPE: PRT
<213> ORGANISM: Artificial Sequence
<220> FEATURE:
<223> OTHER INFORMATION: West Nile virus NS1 antigen; SEQ ID NO: 6 from
      WO 2017/144174

<400> SEQUENCE: 16

Asp Thr Gly Cys Ala Ile Asp Ile Gly Arg Gln Glu Leu Arg Cys Gly
1               5                   10                  15

Ser Gly Val Phe Ile His Asn Asp Val Glu Ala Trp Met Asp Arg Tyr
                20                  25                  30

Lys Phe Tyr Pro Glu Thr Pro Gln Gly Leu Ala Lys Ile Ile Gln Lys
            35                  40                  45

Ala His Ala Glu Gly Val Cys Gly Leu Arg Ser Val Ser Arg Leu Glu
        50                  55                  60

His Gln Met Trp Glu Ala Ile Lys Asp Glu Leu Asn Thr Leu Leu Lys
```

```
            65                  70                  75                  80
        Glu Asn Gly Val Asp Leu Ser Val Val Glu Lys Gln Asn Gly Met
                        85                  90                  95

Tyr Lys Ala Ala Pro Lys Arg Leu Ala Ala Thr Thr Glu Lys Leu Glu
                   100                 105                 110

Met Gly Trp Lys Ala Trp Gly Lys Ser Ile Ile Phe Ala Pro Glu Leu
                   115                 120                 125

Ala Asn Asn Thr Phe Val Ile Asp Gly Pro Glu Thr Glu Glu Cys Pro
                   130                 135                 140

Thr Ala Asn Arg Ala Trp Asn Ser Met Glu Val Glu Asp Phe Gly Phe
        145                 150                 155                 160

Gly Leu Thr Ser Thr Arg Met Phe Leu Arg Ile Arg Glu Thr Asn Thr
                            165                 170                 175

Thr Glu Cys Asp Ser Lys Ile Ile Gly Thr Ala Val Lys Asn Asn Met
                        180                 185                 190

Ala Val His Ser Asp Leu Ser Tyr Trp Ile Glu Ser Gly Leu Asn Asp
                        195                 200                 205

Thr Trp Lys Leu Glu Arg Ala Val Leu Gly Glu Val Lys Ser Cys Thr
                        210                 215                 220

Trp Pro Glu Thr His Thr Leu Trp Gly Asp Gly Val Leu Glu Ser Asp
        225                 230                 235                 240

Leu Ile Ile Pro Ile Thr Leu Ala Gly Pro Arg Ser Asn His Asn Arg
                        245                 250                 255

Arg Pro Gly Tyr Lys Thr Gln Asn Gln Gly Pro Trp Asp Glu Gly Arg
                        260                 265                 270

Val Glu Ile Asp Phe Asp Tyr Cys Pro Gly Thr Thr Val Thr Ile Ser
                        275                 280                 285

Asp Ser Cys Glu His Arg Gly Pro Ala Ala Arg Thr Thr Thr Glu Ser
                        290                 295                 300

Gly Lys Leu Ile Thr Asp Trp Cys Cys Arg Ser Cys Thr Leu Pro Pro
        305                 310                 315                 320

Leu Arg Phe Gln Thr Glu Asn Gly Cys Trp Tyr Gly Met Glu Ile Arg
                        325                 330                 335

Pro Thr Arg His Asp Glu Lys Thr Leu Val Gln Ser Arg Val Asn Ala
                        340                 345                 350

<210> SEQ ID NO 17
<211> LENGTH: 352
<212> TYPE: PRT
<213> ORGANISM: Artificial Sequence
<220> FEATURE:
<223> OTHER INFORMATION: Tick-borne encephalitis virus NS1 antigen; SEQ
      ID NO: 7 from WO 2017/144174

<400> SEQUENCE: 17

Asp Val Gly Cys Ala Val Asp Thr Glu Arg Met Glu Leu Arg Cys Gly
1               5                   10                  15

Glu Gly Leu Val Val Trp Arg Glu Val Ser Glu Trp Tyr Asp Asn Tyr
            20                  25                  30

Ala Tyr Tyr Pro Glu Thr Pro Gly Ala Leu Ala Ser Ala Ile Lys Glu
        35                  40                  45

Thr Phe Glu Glu Gly Thr Cys Gly Ile Val Pro Gln Asn Arg Leu Glu
    50                  55                  60

Met Ala Met Trp Arg Ser Ser Ala Thr Glu Leu Asn Leu Ala Leu Ala
65                  70                  75                  80
```

-continued

Glu Gly Asp Ala Asn Leu Thr Val Val Asp Lys Leu Asp Pro Thr
                85                  90                  95

Asp Tyr Arg Gly Gly Ile Pro Gly Leu Leu Lys Lys Gly Lys Asp Ile
            100                 105                 110

Lys Val Ser Trp Lys Ser Trp Gly His Ser Met Ile Trp Ser Ile Pro
        115                 120                 125

Glu Ala Pro Arg Arg Phe Met Val Gly Thr Glu Gly Ser Ser Glu Cys
    130                 135                 140

Pro Leu Glu Arg Arg Lys Thr Gly Val Phe Thr Val Ala Glu Phe Gly
145                 150                 155                 160

Val Gly Leu Arg Thr Lys Val Phe Leu Asp Phe Arg Gln Glu Ser Thr
                165                 170                 175

His Glu Cys Asp Thr Gly Val Met Gly Ala Ala Val Lys Asn Gly Met
            180                 185                 190

Ala Val His Thr Asp Gln Ser Leu Trp Met Lys Ser Val Arg Asn Asp
        195                 200                 205

Thr Gly Thr Tyr Ile Val Glu Leu Leu Val Thr Asp Leu Arg Asn Cys
    210                 215                 220

Ser Trp Pro Ala Ser His Thr Ile Asp Asn Ala Glu Val Val Asp Ser
225                 230                 235                 240

Glu Leu Phe Leu Pro Ala Ser Leu Ala Gly Pro Arg Ser Trp Tyr Asn
                245                 250                 255

Arg Ile Pro Gly Tyr Ser Glu Gln Val Lys Gly Pro Trp Lys Tyr Ser
            260                 265                 270

Pro Ile Arg Val Thr Arg Glu Glu Cys Pro Gly Thr Arg Val Thr Ile
        275                 280                 285

Asn Ala Asp Cys Asp Lys Arg Gly Ala Ser Val Arg Ser Thr Thr Glu
    290                 295                 300

Ser Gly Lys Val Ile Pro Glu Trp Cys Cys Arg Thr Cys Thr Leu Pro
305                 310                 315                 320

Pro Val Thr Phe Arg Thr Gly Asp Cys Trp Tyr Ala Met Glu Ile
                325                 330                 335

Arg Pro Val His Asp Gln Gly Gly Leu Val Arg Ser Met Val Val Ala
            340                 345                 350

<210> SEQ ID NO 18
<211> LENGTH: 352
<212> TYPE: PRT
<213> ORGANISM: Artificial Sequence
<220> FEATURE:
<223> OTHER INFORMATION: Japanese encephalitis virus NS1 antigen; SEQ ID
      NO: 8 from WO 2017/144174

<400> SEQUENCE: 18

Asp Thr Gly Cys Ala Ile Asp Ile Thr Arg Lys Glu Met Arg Cys Gly
1               5                   10                  15

Ser Gly Ile Phe Val His Asn Asp Val Glu Ala Trp Val Asp Arg Tyr
            20                  25                  30

Lys Tyr Leu Pro Glu Thr Pro Arg Ser Leu Ala Lys Ile Val His Lys
        35                  40                  45

Ala His Gln Glu Gly Val Cys Gly Val Arg Ser Val Thr Arg Leu Glu
    50                  55                  60

His Gln Met Trp Glu Ser Val Arg Asp Glu Leu Asn Val Leu Leu Lys
65                  70                  75                  80

Glu Asn Ala Val Asp Leu Ser Val Val Val Asn Lys Pro Val Gly Arg
                85                  90                  95

```
Tyr Arg Ser Ala Pro Lys Arg Leu Ser Met Thr Gln Glu Lys Phe Glu
                100                 105                 110

Met Gly Trp Lys Ala Trp Gly Lys Ser Ile Leu Phe Ala Pro Glu Leu
            115                 120                 125

Ala Asn Ser Thr Phe Val Val Asp Gly Pro Glu Thr Lys Glu Cys Pro
        130                 135                 140

Asp Glu Arg Arg Ala Trp Asn Ser Met Gln Ile Glu Asp Phe Gly Phe
145                 150                 155                 160

Gly Ile Thr Ser Thr Arg Val Trp Leu Lys Ile Arg Glu Glu Asn Thr
                165                 170                 175

Asp Glu Cys Asp Gly Ala Ile Ile Gly Thr Ala Val Lys Gly His Val
            180                 185                 190

Ala Val His Ser Asp Leu Ser Tyr Trp Ile Glu Ser Arg Leu Asn Asp
        195                 200                 205

Thr Trp Lys Leu Glu Arg Ala Val Phe Gly Glu Val Lys Ser Cys Thr
    210                 215                 220

Trp Pro Glu Thr His Thr Leu Trp Gly Asp Gly Val Glu Glu Ser Glu
225                 230                 235                 240

Leu Ile Ile Pro His Thr Ile Ala Gly Pro Arg Ser Lys His Asn Arg
                245                 250                 255

Arg Glu Gly Tyr Lys Thr Gln Asn Gln Gly Pro Trp Asp Glu Asn Gly
            260                 265                 270

Ile Val Leu Asp Phe Asp Tyr Cys Pro Gly Thr Lys Val Thr Ile Thr
        275                 280                 285

Glu Asp Cys Gly Lys Arg Gly Pro Ser Ile Arg Thr Thr Thr Asp Ser
290                 295                 300

Gly Lys Leu Ile Thr Asp Trp Cys Cys Arg Ser Cys Ser Leu Pro Pro
305                 310                 315                 320

Leu Arg Phe Arg Thr Glu Asn Gly Cys Trp Tyr Gly Met Glu Ile Arg
                325                 330                 335

Pro Val Arg His Asp Glu Thr Thr Leu Val Arg Ser Gln Val Asp Ala
            340                 345                 350

<210> SEQ ID NO 19
<211> LENGTH: 352
<212> TYPE: PRT
<213> ORGANISM: Artificial Sequence
<220> FEATURE:
<223> OTHER INFORMATION: Yellow fever virus NS1 antigen; SEQ ID NO: 9
      from WO 2017/144174

<400> SEQUENCE: 19

Asp Gln Gly Cys Ala Ile Asn Phe Gly Lys Arg Glu Leu Lys Cys Gly
1               5                   10                  15

Asp Gly Ile Phe Ile Phe Arg Asp Ser Asp Asp Trp Leu Asn Lys Tyr
            20                  25                  30

Ser Tyr Tyr Pro Glu Asp Pro Val Lys Leu Ala Ser Ile Val Lys Ala
        35                  40                  45

Ser Phe Glu Glu Gly Lys Cys Gly Leu Asn Ser Val Asp Ser Leu Glu
    50                  55                  60

His Glu Met Trp Arg Ser Arg Ala Asp Glu Ile Asn Ala Ile Leu Glu
65                  70                  75                  80

Glu Asn Glu Val Asp Ile Ser Val Val Val Gln Asp Pro Lys Asn Val
                85                  90                  95

Tyr Gln Arg Gly Thr His Pro Phe Ser Arg Ile Arg Asp Gly Leu Gln
```

```
            100                 105                 110
Tyr Gly Trp Lys Thr Trp Gly Lys Asn Leu Val Phe Ser Pro Gly Arg
        115                 120                 125

Lys Asn Gly Ser Phe Ile Ile Asp Gly Lys Ser Arg Lys Glu Cys Pro
130                 135                 140

Phe Ser Asn Arg Val Trp Asn Ser Phe Gln Ile Glu Glu Phe Gly Thr
145                 150                 155                 160

Gly Val Phe Thr Thr Arg Val Tyr Met Asp Ala Val Phe Glu Tyr Thr
                165                 170                 175

Ile Asp Cys Asp Gly Ser Ile Leu Gly Ala Ala Val Asn Gly Lys Lys
            180                 185                 190

Ser Ala His Gly Ser Pro Thr Phe Trp Met Gly Ser His Glu Val Asn
        195                 200                 205

Gly Thr Trp Met Ile His Thr Leu Glu Ala Leu Asp Tyr Lys Glu Cys
    210                 215                 220

Glu Trp Pro Pro Thr His Thr Ile Gly Thr Ser Val Glu Glu Ser Glu
225                 230                 235                 240

Met Phe Met Pro Arg Ser Ile Gly Gly Pro Val Ser Ser His Asn His
                245                 250                 255

Ile Pro Gly Tyr Lys Val Gln Thr Asn Gly Pro Trp Met Gln Val Pro
            260                 265                 270

Leu Glu Val Lys Arg Glu Ala Cys Pro Gly Thr Ser Val Ile Ile Asp
        275                 280                 285

Gly Asn Cys Asp Gly Arg Gly Lys Ser Thr Arg Ser Thr Thr Asp Ser
    290                 295                 300

Gly Lys Ile Ile Pro Glu Trp Cys Cys Arg Ser Cys Thr Met Pro Pro
305                 310                 315                 320

Val Ser Phe His Gly Ser Asp Gly Cys Trp Tyr Pro Met Glu Ile Arg
                325                 330                 335

Pro Arg Lys Thr His Glu Ser His Leu Val Arg Ser Trp Val Thr Ala
            340                 345                 350

<210> SEQ ID NO 20
<211> LENGTH: 500
<212> TYPE: PRT
<213> ORGANISM: Artificial Sequence
<220> FEATURE:
<223> OTHER INFORMATION: Zika virus envelope glycoprotein; SEQ ID NO: 11
      from WO 2017/144174

<400> SEQUENCE: 20

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110
```

```
Leu Val Thr Cys Ala Lys Phe Thr Cys Ser Lys Lys Met Thr Gly Lys
            115                 120                 125

Ser Ile Gln Pro Glu Asn Leu Glu Tyr Arg Ile Met Leu Ser Val His
130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
    210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
    290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
            340                 345                 350

Arg Leu Ile Thr Ala Asn Pro Val Ile Thr Glu Ser Thr Glu Asn Ser
        355                 360                 365

Lys Met Met Leu Glu Leu Asp Pro Pro Phe Gly Asp Ser Tyr Ile Val
    370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445

Phe Lys Ser Leu Phe Gly Gly Met Ser Trp Phe Ser Gln Ile Leu Ile
    450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
            500

<210> SEQ ID NO 21
<211> LENGTH: 494
<212> TYPE: PRT
```

<213> ORGANISM: Artificial Sequence
<220> FEATURE:
<223> OTHER INFORMATION: Dengue virus 1 envelope glycoprotein; SEQ ID Ala Leu Lys Gln Cys Trp Phe Lys Lys Gly Ser Ile Gly Lys Met
385                 390                 395                 400

Phe Glu Ala Thr Ala Arg Gly Ala Arg Arg Met Ala Ile Leu Gly Asp
            405                 410                 415

Thr Ala Trp Asp Phe Gly Ser Ile Gly Gly Val Phe Thr Ser Val Gly
            420                 425                 430

Lys Leu Val His Gln Val Phe Gly Thr Ala Tyr Gly Val Leu Phe Ser
            435                 440                 445

Gly Val Ser Trp Thr Met Lys Ile Gly Ile Gly Leu Leu Thr Trp
    450                 455                 460

Leu Gly Leu Asn Ser Arg Ser Thr Ser Leu Ser Met Thr Cys Ile Ala
465                 470                 475                 480

Val Gly Met Val Thr Leu Tyr Leu Gly Val Met Val Gln Ala
            485                 490

<210> SEQ ID NO 22
<211> LENGTH: 495
<212> TYPE: PRT
<213> ORGANISM: Artificial Sequence
<220> FEATURE:
<223> OTHER INFORMATION: Dengue virus 2 envelope glycoprotein; SEQ ID
      NO: 13 from WO 2017/144174

<400> SEQUENCE: 22

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Glu Thr
            35                  40                  45

Glu Ala Lys Gln Pro Ala Thr Leu Arg Lys Tyr Cys Ile Glu Ala Lys
    50                  55                  60

Leu Thr Asn Thr Thr Thr Asp Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Lys Gly Lys
            115                 120                 125

Val Val Gln Pro Glu Asn Leu Glu Tyr Thr Ile Val Ile Thr Pro His
    130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
            195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

```
Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
                340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Ile Gly Val Glu Pro
        370                 375                 380

Gly Gln Leu Lys Leu Asn Trp Phe Lys Lys Gly Ser Ser Ile Gly Gln
385                 390                 395                 400

Met Ile Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
        435                 440                 445

Ser Gly Val Ser Trp Ile Met Lys Ile Leu Ile Gly Val Ile Ile Thr
    450                 455                 460

Trp Ile Gly Met Asn Ser Arg Ser Thr Ser Leu Ser Val Ser Leu Val
465                 470                 475                 480

Leu Val Gly Val Val Thr Leu Tyr Leu Gly Val Met Val Gln Ala
                485                 490                 495

<210> SEQ ID NO 23
<211> LENGTH: 493
<212> TYPE: PRT
<213> ORGANISM: Artificial Sequence
<220> FEATURE:
<223> OTHER INFORMATION: Dengue virus 3 envelope glycoprotein; SEQ ID
      NO: 14 from WO 2017/144174

<400> SEQUENCE: 23

Met Ar

```
                115                 120                 125
Val Val Gln His Glu Asn Leu Lys Tyr Thr Val Ile Ile Thr Val His
        130                 135                 140

Thr Gly Asp Gln His Gln Val Gly Asn Glu Thr Gln Gly Val Thr Ala
145                 150                 155                 160

Glu Ile Thr Ser Gln Ala Ser Thr Ala Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Lys Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Thr Ser Gly
            260                 265                 270

Gly Thr Ser Ile Phe Ala Gly His Leu Lys Cys Arg Leu Lys Met Asp
        275                 280                 285

Lys Leu Lys Leu Lys Gly Met Ser Tyr Ala Met Cys Leu Asn Thr Phe
    290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
        355                 360                 365

Pro Pro Phe Gly Glu Ser Asn Ile Val Ile Gly Ile Gly Asp Lys Ala
    370                 375                 380

Leu Lys Ile Asn Trp Tyr Arg Lys Gly Ser Ser Ile Gly Lys Met Phe
385                 390                 395                 400

Glu Ala Thr Ala Arg Gly Ala Arg Arg Met Ala Ile Leu Gly Asp Thr
                405                 410                 415

Ala Trp Asp Phe Gly Ser Val Gly Gly Val Leu Asn Ser Leu Gly Lys
            420                 425                 430

Met Val His Gln Ile Phe Gly Ser Ala Tyr Thr Ala Leu Phe Ser Gly
        435                 440                 445

Val Ser Trp Ile Met Lys Ile Gly Ile Gly Val Leu Leu Thr Trp Ile
    450                 455                 460

Gly Leu Asn Ser Lys Asn Thr Ser Met Ser Phe Ser Cys Ile Ala Ile
465                 470                 475                 480

Gly Ile Ile Thr Leu Tyr Leu Gly Val Val Val Gln Ala
                485                 490
```

<210> SEQ ID NO 24
<211> LENGTH: 495
<212> TYPE: PRT
<213> ORGANISM: Artificial Sequence
<220> FEATURE:
<223> OTHER INFORMATION: Dengue virus 4 envelope glycoprotein; SEQ ID
      NO: 15 from WO 2017/144174

<400> SEQUENCE: 24

```
Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Thr Lys Thr
        35                  40                  45

Thr Ala Lys Glu Val Ala Leu Leu Arg Thr Tyr Cys Ile Glu Ala Ser
50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Thr Val His
130                 135                 140

Asn Gly Asp Thr His Ala Val Gly Asn Asp Thr Ser Asn His Gly Val
145                 150                 155                 160

Thr Ala Met Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Thr Trp Leu Val
        195                 200                 205

His Lys Gln Trp Phe Leu Asp Leu Pro Leu Pro Trp Thr Ala Gly Ala
210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Ala Gly His Leu Lys Cys Lys Val Arg
        275                 280                 285

Met Glu Lys Leu Arg Ile Lys Gly Met Ser Tyr Thr Met Cys Ser Gly
290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
            340                 345                 350

Ser Ser Thr Pro Leu Ala Glu Asn Thr Asn Ser Val Thr Asn Ile Glu
        355                 360                 365

Leu Glu Pro Pro Phe Gly Asp Ser Tyr Ile Val Ile Gly Val Gly Asn
370                 375                 380

Ser Ala Leu Thr Leu His Trp Phe Arg Lys Gly Ser Ser Ile Gly Lys
385                 390                 395                 400

Met Phe Glu Ser Thr Tyr Arg Gly Ala Lys Arg Met Ala Ile Leu Gly
```

-continued

```
                    405                 410                 415
Glu Thr Ala Trp Asp Phe Gly Ser Val Gly Gly Leu Phe Thr Ser Leu
                420                 425                 430

Gly Lys Ala Val His Gln Val Phe Gly Ser Val Tyr Thr Thr Met Phe
            435                 440                 445

Gly Gly Val Ser Trp Met Ile Arg Ile Leu Ile Gly Phe Leu Val Leu
        450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495

<210> SEQ ID NO 25
<211> LENGTH: 497
<212> TYPE: PRT
<213> ORGANISM: Artificial Sequence
<220> FEATURE:
<223> OTHER INFORMATION: West Nile virus envelope glycoprotein; SEQ ID
      NO: 16 from WO 2017/144174

<400> SEQUENCE: 25

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Asp Val Arg Ser Tyr Cys Tyr Leu Ala Ser
    50                  55                  60

Val Ser Asp Leu Ser Thr Arg Ala Ala Cys Pro Thr Met Gly Glu Ala
65                  70                  75                  80

His Asn Glu Lys Arg Ala Asp Pro Ala Phe Val Cys Lys Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Thr Thr Lys Ala Thr Gly Trp
        115                 120                 125

Ile Ile Gln Lys Glu Asn Ile Lys Tyr Glu Val Ala Ile Phe Val His
    130                 135                 140

Gly Pro Thr Thr Val Glu Ser His Gly Lys Ile Gly Ala Thr Gln Ala
145                 150                 155                 160

Gly Arg Phe Ser Ile Thr Pro Ser Ala Pro Ser Tyr Thr Leu Lys Leu
                165                 170                 175

Gly Glu Tyr Gly Glu Val Thr Val Asp Cys Glu Pro Arg Ser Gly Ile
            180                 185                 190

Asp Thr Ser Ala Tyr Tyr Val Met Ser Val Gly Glu Lys Ser Phe Leu
        195                 200                 205

Val His Arg Glu Trp Phe Met Asp Leu Asn Leu Pro Trp Ser Ser Ala
    210                 215                 220

Gly Ser Thr Thr Trp Arg Asn Arg Glu Thr Leu Met Glu Phe Glu Glu
225                 230                 235                 240

Pro His Ala Thr Lys Gln Ser Val Val Ala Leu Gly Ser Gln Glu Gly
                245                 250                 255

Ala Leu His Gln Ala Leu Ala Gly Ala Ile Pro Val Glu Phe Ser Ser
            260                 265                 270
```

```
Asn Thr Val Lys Leu Thr Ser Gly His Leu Lys Cys Arg Val Lys Met
            275                 280                 285

Glu Lys Leu Gln Leu Lys Gly Thr Thr Tyr Gly Val Cys Ser Lys Ala
    290                 295                 300

Phe Lys Phe Ala Arg Thr Pro Ala Asp Thr Gly His Gly Thr Val Val
305                 310                 315                 320

Leu Glu Leu Gln Tyr Thr Gly Thr Asp Gly Pro Cys Lys Val Pro Ile
                325                 330                 335

Ser Ser Val Ala Ser Leu Asn Asp Leu Thr Pro Val Gly Arg Leu Val
                340                 345                 350

Thr Val Asn Pro Phe Val Ser Val Ala Thr Ala Asn Ser Lys Val Leu
            355                 360                 365

Ile Glu Leu Glu Pro Pro Phe Gly Asp Ser Tyr Ile Val Val Gly Arg
        370                 375                 380

Gly Glu Gln Gln Ile Asn His His Trp His Lys Ser Gly Ser Ser Ile
385                 390                 395                 400

Gly Lys Ala Phe Thr Thr Thr Leu Arg Gly Ala Gln Arg Leu Ala Ala
                405                 410                 415

Leu Gly Asp Thr Ala Trp Asp Phe Gly Ser Val Gly Gly Val Phe Thr
                420                 425                 430

Ser Val Gly Lys Ala Ile His Gln Val Phe Gly Gly Ala Phe Arg Ser
        435                 440                 445

Leu Phe Gly Gly Met Ser Trp Ile Thr Gln Gly Leu Leu Gly Ala Leu
    450                 455                 460

Leu Leu Trp Met Gly Ile Asn Ala Arg Asp Arg Ser Ile Ala Met Thr
465                 470                 475                 480

Phe Leu Ala Val Gly Gly Val Leu Leu Phe Leu Ser Val Asn Val His
                485                 490                 495

Ala

<210> SEQ ID NO 26
<211> LENGTH: 496
<212> TYPE: PRT
<213> ORGANISM: Artificial Sequence
<220> FEATURE:
<223> OTHER INFORMATION: Tick-borne encephalitis virus envelope
      glycoprotein; SEQ ID NO: 17 from WO 2017/144174

<400> SEQUENCE: 26

Ser Arg Cys Thr His Leu Glu Asn Arg Asp Phe Val Thr Gly Thr Gln
1               5                   10                  15

Gly Thr Thr Arg Val Thr Leu Val Leu Glu Leu Gly Gly Cys Val Thr
                20                  25                  30

Ile Thr Ala Glu Gly Lys Pro Ser Met Asp Val Trp Leu Asp Ala Ile
            35                  40                  45

Tyr Gln Glu Lys Pro Ala Lys Thr Arg Glu Tyr Cys Leu His Ala Lys
        50                  55                  60

Leu Ser Asp Thr Lys Val Ala Ala Arg Cys Pro Thr Met Gly Pro Ala
65                  70                  75                  80

Thr Leu Thr Glu Glu His Gln Gly Gly Thr Val Cys Lys Arg Asp Gln
                85                  90                  95

Ser Asp Arg Gly Trp Gly Asn His Cys Gly Leu Phe Gly Lys Gly Ser
                100                 105                 110

Ile Val Ala Cys Val Lys Ala Ala Cys Glu Ala Lys Lys Lys Ala Thr
            115                 120                 125
```

```
Gly His Val Tyr Asp Ala Asn Arg Ile Val Tyr Thr Val Lys Val Glu
    130                 135                 140

Pro His Thr Gly Asp Tyr Val Ala Ala Asn Glu Thr His Ser Gly Arg
145                 150                 155                 160

Lys Thr Ala Ser Phe Thr Val Ser Ser Glu Lys Thr Ile Leu Thr Met
                165                 170                 175

Gly Glu Tyr Gly Asp Val Ser Leu Leu Cys Arg Val Ala Ser Gly Val
            180                 185                 190

Asp Leu Ala Gln Thr Val Ile Leu Glu Leu Asp Lys Thr Val Glu His
        195                 200                 205

Leu Pro Thr Ala Trp Gln Val His Arg Asp Trp Phe Asn Asp Leu Ala
210                 215                 220

Leu Pro Trp Lys His Glu Gly Ala Gln Asn Trp Asn Asn Ala Glu Arg
225                 230                 235                 240

Leu Val Glu Phe Gly Ala Pro His Ala Val Lys Met Asp Val Tyr Asn
                245                 250                 255

Leu Gly Asp Gln Thr Gly Val Leu Leu Lys Ala Leu Ala Gly Val Pro
            260                 265                 270

Val Ala His Ile Glu Gly Thr Lys Tyr His Leu Lys Ser Gly His Val
        275                 280                 285

Thr Cys Glu Val Gly Leu Glu Lys Leu Lys Met Lys Gly Leu Thr Tyr
290                 295                 300

Thr Met Cys Asp Lys Thr Lys Phe Thr Trp Lys Arg Ala Pro Thr Asp
305                 310                 315                 320

Ser Gly His Asp Thr Val Val Met Glu Val Thr Phe Ser Gly Thr Lys
                325                 330                 335

Pro Cys Arg Ile Pro Val Arg Ala Val Ala His Gly Ser Pro Asp Val
            340                 345                 350

Asn Val Ala Met Leu Ile Thr Pro Asn Pro Thr Ile Glu Asn Asn Gly
        355                 360                 365

Gly Gly Phe Ile Glu Met Gln Leu Pro Pro Gly Asp Asn Ile Ile Tyr
370                 375                 380

Val Gly Glu Leu Ser His Gln Trp Phe Gln Lys Gly Ser Ser Ile Gly
385                 390                 395                 400

Arg Val Phe Gln Lys Thr Lys Lys Gly Ile Glu Arg Leu Thr Val Ile
                405                 410                 415

Gly Glu His Ala Trp Asp Phe Gly Ser Ala Gly Gly Phe Leu Ser Ser
            420                 425                 430

Ile Gly Lys Ala Val His Thr Val Leu Gly Gly Ala Phe Asn Ser Ile
        435                 440                 445

Phe Gly Gly Val Gly Phe Leu Pro Lys Leu Leu Leu Gly Val Ala Leu
450                 455                 460

Ala Trp Leu Gly Leu Asn Met Arg Asn Pro Thr Met Ser Met Ser Phe
465                 470                 475                 480

Leu Leu Ala Gly Gly Leu Val Leu Ala Met Thr Leu Gly Val Gly Ala
                485                 490                 495

<210> SEQ ID NO 27
<211> LENGTH: 500
<212> TYPE: PRT
<213> ORGANISM: Artificial Sequence
<220> FEATURE:
<223> OTHER INFORMATION: Japanese encephalitis virus envelope
      glycoprotein; SEQ ID NO: 18 from WO 2017/144174

<400> SEQUENCE: 27
```

-continued

```
Phe Asn Cys Leu Gly Met Gly Asn Arg Asp Phe Ile Glu Gly Ala Ser
1               5                   10                  15
Gly Ala Thr Trp Val Asp Leu Val Leu Glu Gly Asp Ser Cys Leu Thr
                20                  25                  30
Ile Met Ala Asn Asp Lys Pro Thr Leu Asp Val Arg Met Ile Asn Ile
            35                  40                  45
Glu Ala Ser Gln Leu Ala Glu Val Arg Ser Tyr Cys Tyr His Ala Ser
        50                  55                  60
Val Thr Asp Ile Ser Thr Val Ala Arg Cys Pro Thr Thr Gly Glu Ala
65                  70                  75                  80
His Asn Glu Lys Arg Ala Asp Ser Ser Tyr Val Cys Lys Gln Gly Phe
                85                  90                  95
Thr Asp Arg Gly Trp Gly Asn Gly Cys Gly Leu Phe Gly Lys Gly Ser
                100                 105                 110
Ile Asp Thr Cys Ala Lys Phe Ser Cys Thr Ser Lys Ala Ile Gly Arg
            115                 120                 125
Thr Ile Gln Pro Glu Asn Ile Lys Tyr Glu Val Gly Ile Phe Val His
        130                 135                 140
Gly Thr Thr Thr Ser Glu Asn His Gly Asn Tyr Ser Ala Gln Val Gly
145                 150                 155                 160
Ala Ser Gln Ala Ala Lys Phe Thr Val Thr Pro Asn Ala Pro Ser Ile
                165                 170                 175
Thr Leu Lys Leu Gly Asp Tyr Gly Glu Val Thr Leu Asp Cys Glu Pro
                180                 185                 190
Arg Ser Gly Leu Asn Thr Glu Ala Phe Tyr Val Met Thr Val Gly Ser
            195                 200                 205
Lys Ser Phe Leu Val His Arg Glu Trp Phe His Asp Leu Ala Leu Pro
        210                 215                 220
Trp Thr Ser Pro Ser Ser Thr Ala Trp Arg Asn Arg Glu Leu Leu Met
225                 230                 235                 240
Glu Phe Glu Glu Ala His Ala Thr Lys Gln Ser Val Val Ala Leu Gly
                245                 250                 255
Ser Gln Glu Gly Gly Leu His Gln Ala Leu Ala Gly Ala Ile Val Val
            260                 265                 270
Glu Tyr Ser Ser Ser Val Lys Leu Thr Ser Gly His Leu Lys Cys Arg
        275                 280                 285
Leu Lys Met Asp Lys Leu Ala Leu Lys Gly Thr Thr Tyr Gly Met Cys
    290                 295                 300
Thr Glu Lys Phe Ser Phe Ala Lys Asn Pro Ala Asp Thr Gly His Gly
305                 310                 315                 320
Thr Val Val Ile Glu Leu Ser Tyr Ser Gly Ser Asp Gly Pro Cys Lys
                325                 330                 335
Ile Pro Ile Val Ser Val Ala Ser Leu Asn Asp Met Thr Pro Val Gly
            340                 345                 350
Arg Leu Val Thr Val Asn Pro Phe Val Ala Thr Ser Ser Ala Asn Ser
        355                 360                 365
Lys Val Leu Val Glu Met Glu Pro Pro Phe Gly Asp Ser Tyr Ile Val
    370                 375                 380
Val Gly Arg Gly Asp Lys Gln Ile Asn His His Trp His Lys Ala Gly
385                 390                 395                 400
Ser Thr Leu Gly Lys Ala Phe Ser Thr Thr Leu Lys Gly Ala Gln Arg
                405                 410                 415
```

```
Leu Ala Ala Leu Gly Asp Thr Ala Trp Asp Phe Gly Ser Ile Gly Gly
                420                 425                 430

Val Phe Asn Ser Ile Gly Lys Ala Val His Gln Val Phe Gly Gly Ala
            435                 440                 445

Phe Arg Thr Leu Phe Gly Gly Met Ser Trp Ile Thr Gln Gly Leu Met
        450                 455                 460

Gly Ala Leu Leu Leu Trp Met Gly Val Asn Ala Arg Asp Arg Ser Ile
465                 470                 475                 480

Ala Leu Ala Phe Leu Ala Thr Gly Gly Val Leu Val Phe Leu Ala Thr
                485                 490                 495

Asn Val His Ala
            500

<210> SEQ ID NO 28
<211> LENGTH: 493
<212> TYPE: PRT
<213> ORGANISM: Artificial Sequence
<220> FEATURE:
<223> OTHER INFORMATION: Yellow fever virus envelope glycoprotein; SEQ
      ID NO: 27 from WO 2017/144174

<400> SEQUENCE: 28

Ala His Cys Ile Gly Ile Thr Asp Arg Asp Phe Ile Glu Gly Val His
1               5                   10                  15

Gly Gly Thr Trp Val Ser Ala Thr Leu Glu Gln Asp Lys Cys Val Thr
            20                  25                  30

Val Met Ala Pro Asp Lys Pro Ser Leu Asp Ile Ser Leu Glu Thr Val
        35                  40                  45

Ala Ile Asp Gly Pro Ala Glu Ala Arg Lys Val Cys Tyr Asn Ala Val
    50                  55                  60

Leu Thr His Val Lys Ile Asn Asp Lys Cys Pro Ser Thr Gly Glu Ala
65                  70                  75                  80

His Leu Ala Glu Glu Asn Glu Gly Asp Asn Ala Cys Lys Arg Thr Tyr
                85                  90                  95

Ser Asp Arg Gly Trp Gly Asn Gly Cys Gly Leu Phe Gly Lys Gly Ser
            100                 105                 110

Ile Val Ala Cys Ala Lys Phe Thr Cys Ala Lys Ser Met Ser Leu Phe
        115                 120                 125

Glu Val Asp Gln Thr Lys Ile Gln Tyr Val Ile Arg Ala Gln Leu His
    130                 135                 140

Val Gly Ala Lys Gln Glu Asn Trp Asn Thr Asp Ile Lys Thr Leu Lys
145                 150                 155                 160

Phe Asp Ala Leu Ser Gly Ser Gln Glu Ala Glu Phe Thr Gly Tyr Gly
                165                 170                 175

Lys Ala Thr Leu Glu Cys Gln Val Gln Thr Ala Val Asp Phe Gly Asn
            180                 185                 190

Ser Tyr Ile Ala Glu Met Glu Lys Glu Ser Trp Ile Val Asp Arg Gln
        195                 200                 205

Trp Ala Gln Asp Leu Thr Leu Pro Trp Gln Ser Gly Ser Gly Gly Val
    210                 215                 220

Trp Arg Glu Met His His Leu Val Glu Phe Glu Pro Pro His Ala Ala
225                 230                 235                 240

Thr Ile Arg Val Leu Ala Leu Gly Asn Gln Glu Gly Ser Leu Lys Thr
                245                 250                 255

Ala Leu Thr Gly Ala Met Arg Val Thr Lys Asp Thr Asn Asp Asn Asn
            260                 265                 270
```

Leu Tyr Lys Leu His Gly Gly His Val Ser Cys Arg Val Lys Leu Ser
              275                 280                 285

Ala Leu Thr Leu Lys Gly Thr Ser Tyr Lys Met Cys Thr Asp Lys Met
            290                 295                 300

Ser Phe Val Lys Asn Pro Thr Asp Thr Gly His Gly Thr Val Val Met
305                 310                 315                 320

Gln Val Lys Val Pro Lys Gly Ala Pro Cys Lys Ile Pro Val Ile Val
                325                 330                 335

Ala Asp Asp Leu Thr Ala Ala Ile Asn Lys Gly Ile Leu Val Thr Val
                340                 345                 350

Asn Pro Ile Ala Ser Thr Asn Asp Asp Glu Val Leu Ile Glu Val Asn
                355                 360                 365

Pro Pro Phe Gly Asp Ser Tyr Ile Ile Val Gly Thr Gly Asp Ser Arg
        370                 375                 380

Leu Thr Tyr Gln Trp His Lys Glu Gly Ser Ser Ile Gly Lys Leu Phe
385                 390                 395                 400

Thr Gln Thr Met Lys Gly Ala Glu Arg Leu Ala Val Met Gly Asp Ala
                405                 410                 415

Ala Trp Asp Phe Ser Ser Ala Gly Gly Phe Phe Thr Ser Val Gly Lys
            420                 425                 430

Gly Ile His Thr Val Phe Gly Ser Ala Phe Gln Gly Leu Phe Gly Gly
        435                 440                 445

Leu Asn Trp Ile Thr Lys Val Ile Met Gly Ala Val Leu Ile Trp Val
    450                 455                 460

Gly Ile Asn Thr Arg Asn Met Thr Met Ser Met Ser Met Ile Leu Val
465                 470                 475                 480

Gly Val Ile Met Met Phe Leu Ser Leu Gly Val Gly Ala
                485                 490

<210> SEQ ID NO 29
<211> LENGTH: 353
<212> TYPE: PRT
<213> ORGANISM: Artificial Sequence
<220> FEATURE:
<223> OTHER INFORMATION: Powassan virus NS1 antigen; SEQ ID NO: 19 from
      WO 2017/144174

<400> SEQUENCE: 29

Asp Tyr Gly Cys Ala Ile Asp Pro Glu Arg Met Glu Ile Arg Cys Gly
1               5                   10                  15

Glu Gly Leu Val Val Trp Lys Glu Val Ser Glu Trp Tyr Asp Gly Tyr
                20                  25                  30

Ala Tyr His Pro Glu Ser Pro Asp Thr Leu Ala Gln Ala Leu Arg Glu
            35                  40                  45

Ala Phe Glu Arg Gly Val Cys Gly Val Val Pro Gln Asn Arg Leu Glu
        50                  55                  60

Met Ala Met Trp Arg Ser Thr Ala Pro Glu Leu Asn Leu Val Leu Ser
65                  70                  75                  80

Glu Gly Glu Ala Asn Leu Thr Ile Val Val Asp Lys Thr Asp Pro Ala
                85                  90                  95

Asp Tyr Arg Gly Gly Thr Pro Met Val Leu Lys Lys Thr Gly Lys Glu
                100                 105                 110

Ser Lys Val Ser Trp Lys Ser Trp Gly Lys Ser Ile Leu Trp Ser Val
            115                 120                 125

Pro Asp Ser Pro Arg Arg Met Met Met Gly Val Asp Gly Val Gly Glu

```
                130             135             140
Cys Pro Leu Tyr Arg Arg Ala Thr Gly Val Phe Thr Val Ala Glu Phe
145                 150                 155                 160

Gly Val Gly Leu Arg Thr Lys Val Phe Leu Asp Leu Arg Gly Glu Ala
                165                 170                 175

Ser Lys Glu Cys Asp Thr Gly Val Met Gly Ala Ala Val Lys Asn Gly
            180                 185                 190

Lys Ala Ile His Thr Asp Gln Ser Met Trp Met Ser Ser Phe Arg Asn
            195                 200                 205

Asp Thr Gly Thr Tyr Ile His Glu Leu Ile Leu Thr Asp Leu Arg Asn
            210                 215                 220

Cys Thr Trp Pro Ala Ser His Thr Ile Asp Asn Asp Gly Val Leu Asp
225                 230                 235                 240

Ser His Leu Phe Leu Pro Val Thr Leu Ala Gly Pro Arg Ser Lys Tyr
                245                 250                 255

Asn Arg Ile Pro Gly Tyr Ser Glu Gln Val Arg Gly Pro Trp Asp Gln
                260                 265                 270

Thr Pro Leu Arg Val Val Arg Asp His Cys Pro Gly Thr Ser Val Arg
                275                 280                 285

Ile Asp Ser His Cys Asp Lys Arg Gly Ala Ser Val Arg Ser Thr Thr
            290                 295                 300

Glu Ser Gly Lys Ile Ile Pro Glu Trp Cys Cys Arg Ala Cys Glu Leu
305                 310                 315                 320

Pro Pro Val Thr Phe Arg Ser Gly Thr Asp Cys Trp Tyr Ala Met Glu
                325                 330                 335

Ile Arg Pro Val His Ser Gln Gly Gly Leu Val Arg Ser Met Val Val
                340                 345                 350

Ala
```